US006521420B1

(12) United States Patent
Herman et al.

(10) Patent No.: US 6,521,420 B1
(45) Date of Patent: Feb. 18, 2003

(54) HYPERTENSION ASSOCIATED TRANSCRIPTION FACTORS AND USES THEREFOR

(75) Inventors: Ira M. Herman, Newton, MA (US); Greg J. Sieczkiewicz, Conventry, RI (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/389,831

(22) Filed: Sep. 3, 1999

Related U.S. Application Data

(60) Provisional application No. 60/099,289, filed on Sep. 4, 1998.

(51) Int. Cl.[7] .......................... C12P 21/06; C07H 17/00; C07K 14/00
(52) U.S. Cl. ................ 435/69.1; 435/320.1; 435/252.3; 435/325; 536/23.1; 530/300; 530/350
(58) Field of Search ......................... 536/23.1; 435/69.1, 435/320.1, 252.3, 325; 530/300, 350

(56) References Cited

PUBLICATIONS

Blume, Annegret et al. "Increased Brain Transcription Factor Expression by Angiotensin in Genetic Hypertension" *Hypertension* 29(2):592–98 (1997).
Abboud, H.E. et al., "Production of platelet–derived growth factor–like protein by rat mesangial cells in culture," *J. Clin. Invest.* 80:675–83 (1987).
Barbaux, S. et al., "Donor splice–site mutations in WT1 are responsible for Frasier syndrome," *Nat Genet.* 17(4):467–70 (1997).
Biron, P. et al., "Familial aggregation of blood pressure in 558 adopted children," *Can. Med. Assoc.* 115:773–774 (1976).
Brennan, P.J. et al., "Seasonal variation in arterial blood pressure," *Br. Med. J.* 285:19–23 (1982).
Bruening, W. et al., "A non–AUG translational initiation event generates novel WT1 isoforms," *J Biol Chem.*, 271(15):8646–54 (1996).
Campese, V.M., "Salt sensitivity in hypertension. Renal and cardiovascular implications," *Hypertension*, 23:531–550.
Choi, Y. et al., "Renovascular hypertension in children with moyamoya disease," *J. Pediatricx*, 131:258–263 (1997).
Christian, J.C., "Twin studies of blood pressure," In *Children's blood pressure*, L.J.a.R.M.L. Filer, editor. Ross Laboratories, Columbus, OH, 51–55 (1985).
Chua, B.H. et al., "Regulation of endothelin–1 mRNA by angiotensin II in rat heart endothelial cells," *Biochem. Biophys. Acta*, 1178:201–6 (1993).
Cortes, P. et al., "Glomerular hypertension and progressive renal disease: the interplay of mesangial cell stretch, cytokine formation and extracellular matrix synthesis," *Contrib Nephrol.*, 118:229–33 (1996).

DeMey, J.G. et al., "Endothelium–dependent reactivity in resistance arteries," *Prog. Appl. Microcirc.*, 88:181–7 (1985).
De Meyer, G.R. et al., "Vascular endothelial dysfunction," *Prog in Cardiovascular diseases*, 39:325–42.
Deng, Y. et al., "Cosegregation of blood pressure with angiotensin converting enzyme and atrial natriuretic peptide receptor genes using Dahl salt–sensitive rats," *Nature Genetics*, 1:267–72 (1992).
Drash, A. et al., "A syndrome of pseudohermaphroditism, Wilm's tumor, hypertension, and degenerative renal disease," *J. Pediatr.*, 76:585–93 (1970).
Dzau, V.J. et al., "Genetic models of human vascular disease," *Circulation*,91:521–31 (1995).
Floege, J. et al., "Glomerular cell proliferation and PDGF expression precede glomerulosclerosis in the remnant kidney model," *Kidney Int.*, 41:297–309 (1992a).
Floege, J. et al., "Heparin suppresses mesangial cell proliferation and matrix expansion in experimental mesangioproliferative glomerulonephritis," *kidney Int.*, 43:369–80 (1993a).
Floege, J. et al., "Factors involved in the regulation of mesangial cell proliferation in vitro and in vivo," *Kidney Int. Suppl*, 39:S47–54 (1993b).
Floege, J. et al., "Mesangial cells in the pathology of progressive glomerular disease in animal models," *Clinical Investigator*, 70:857–64 (1992b).
Gauer, S. et al., "Adhesion molecules in the glomerular mesangium," *Kidney Int.*, 51(5):1447–53 (1997).
Gordon, R.D. et al., In Hypertension: Pathophysiology, diagnosis and management, J.L.a.B.M. Brenner, editor, Raven, New York, NY, 2111–23 (1995).
Habib, R. et al., The nephropathy associated with male pseudohermaphroditism and Wilms' tumor (Drash syndrome): a distinctive glomerular lesion—report of 10 cases. *Clin Nephrol.*, 24(6):269–78 (1985).
Hamet, P. et al., "Restriction fragment length polymorphism of hsp70 gene, localized in the RT1 complex is associated with hypertension in spontaneously hypertensive rats," *Hypertension.*, 19(6 Pt 2):611–4 (1992).

(List continued on next page.)

Primary Examiner—Karen Cochrane Carlson
(74) Attorney, Agent, or Firm—Lahive & Cockfield, LLP; Amy E. Mandragouras; Maria Laccotripe Zacharakis

(57) ABSTRACT

The invention provides isolated nucleic acids molecules, designated HATF-1 and HRP-1 nucleic acid molecules, which are differentially expressed in hypertensive humans, rats, and mice. The invention also provides antisense nucleic acid molecules, recombinant expression vectors containing HATF-1 or HRP-1 nucleic acid molecules, host cells into which the expression vectors have been introduced, and nonhuman transgenic animals in which an HATF-1 or HRP-1 gene has been introduced or disrupted. The invention still further provides isolated HATF-1 and HRP-1 proteins, fusion proteins, antigenic peptides and anti-HATF-1 and anti-HRP-1 antibodies. Diagnostic methods utilizing compositions of the invention are also provided.

14 Claims, 14 Drawing Sheets

OTHER PUBLICATIONS

Healy, M.A. et al., "Density–dependent accumulation of basic fibroblast growth factor in the subendothelial matrix," *Eur. J. Cell. Biol.* 59:56–67 (1992).

Heistad, D.D. et al., "Cerebral vascular changes during chronic hypertension: good guys and bad guys," *J Hypertens Suppl.*, 10(7):S71–5 (1992).

Herman, I.M., "Developing probes and methods for morphologic and biochemical analyses of cytoskeletal elements in vascular cells," *CRC Crit. Anat. Sci.*, 1:133–48 (1988).

Herman, I.M. et al., "In situ analysis of microvascular pericytes in hypertensive rat brains," *Tissue cell*, 20:1–12 (1988).

Herman, I.M. et al., "Characterization of microvascular cell cultures from normorensive and hypertensive rat brains:pericyteendothelial cell interactions in vitro," *Tissue cell*, 19:197–206 (1987).

Hewitt, S.M. et al., Differential function of Wilm's tumor gene WT1 splice isoforms in transcriptional regulation, *J. Biol. Chem.*, 271:8588–92 (1996).

Hilbert, P, et al., "Chromosomal mapping of two genetic loci associated with blood–pressure regulation in hereditary hypertensive rats," *Nature*, 353:521–9 (1991).

Hubner, N. et al., "Genetics in arterial hypertension— clinical and experimental aspects," *Herz.*, 20(5):309–14 (1995).

Jacob, H.J. et al., "Genetic mapping of a gene causing hypertension in stroke–prone spontaneously hypertensive rat," *Cell*, 67(1):213–24 (1991).

Jeunemaitre, X, et al, "Absence of linkage betweeen the angiotensin converting enzyme locus and human essential hypertension," *Nat. Genet.* 1(1):72–5 (1992).

Jeunemaitre, X, et al., "Molecular basis of human hypertension: role of angiotensinogen," *Cell,* 71(1):169–80 (1992).

Johnson et al., "Genetic divergence between the Wistar– Kyoto rat and the spontaneously hypertensive rat," *Hypertension.* 1992 May; 19(5):425–7.

Kaname, S. et al., "Autocrine secretion of transforming growth factor–beta in cultured rat mesangial cells," *Kidney Int.* 1992 Dec; 42(6):1319–27.

Katsuya, T. et al., "A neuropeptide Y locus on chromosome 4 cosegregates with blood pressure in the spontaneously hypertensive rat," *Biochem Biophys Res Commun.* Apr. 15, 1993;192(1):261–7.

Kohno, M. et al., "Angiotensin II stimulates endothelin–1 secretion in cultured rat mesangial cells," *Kidney Int.* 1992 Oct.;42(4):860–6.

Krieger, J.E. et al., "Genetic dissection of hypertension in the spontaneously hypertensive rat," *J Hypertens.,* 12:S66 (1994).

Krieger, J.E. et al., "Evidence for a mutation in the promoter region of the ACE gene SHR–SP vs. WKY," *Hypertension,* 20:412 (1992).

Kunes, J. et al., "Influence of environmental temperature on blood pressure of hypertensive patients in Montreal," *Am J Hypertens.* 1991 May;4(5 Pt 1):422–6.

Largo, R. et al., "Endothelin–1 upregulation in the kidney of uninephrectomized spontaneously hypertensive rats and its modification by the angiotensin–converting enzyme inhibitor quinapril," Hypertension, 1997 May;29(5):1178–85.

Liang, P. et al., "Differential display of eukaryotic messenger RNA by means of the polymerase chain reaction," *Science,* Aug. 14, 1992;257(5072):967–71.

Lifton, R.P., "Genetic determinants of human hypertension," *Proc Natl Acad Sci U S A.* Sep. 12, 1995;92(19):8545–51.

Lifton, R.P., "Molecular genetics of human blood pressure variation," *Science.* May 3, 1996;272(5262):676–80.

Lifton, R.P., "A chimaeric 11 beta–hydroxylase/aldosterone synthase gene causes glucocorticoid–remediable aldosteronism and human hypertension," *Nature.* Jan. 16, 1992;355(6357):262–5.

Linder, L. et al., "Indirect evidence for release of endothelium–derived relaxing factor in human forearm circulation in vivo. Blunted reponse in essential hypertension," *Circulation* 1990 Jun.; 81(6):1762–7.

Lindpainter, K. et al., "Molecular genetics of the SA–gene cosegregation with hypertension and mapping to rat chromosome 1," *J Hypertens.* Jan. 1993;11(1):19–23.

Longini, I.M. et al., "Environmental and genetic sources of familial aggregation of blood pressure in Tecumseh, Michigan," *Am J Epidemiol.* Jul. 1984;120(1):131–44.

Luscher, T.F., "Heterogeneity of endothelial dysfunction in hypertension," *Eur Heart J.* 1992 Sep.; 13 Suppl D:50–5.

Luscher, T.F. et al., "Endothelium–dependent contractions to acetylcholine in the aorta of the spontaneously hypertensive rat," *Hypertension.* 1986 Apr.;8(4):344–8.

MacGregor, G.A., "Sodium is more important than calcium in essential hypertension," *Hypertension.* 1985 Jul.–Aug.; 7(4):628–40.

Malo, D. et al., "Thermosensitivity, a possible new locus involved in genetic hypertension," *Hypertension.* 1989 Aug.; 14(2):121–8.

Mayhan, W.G. et al., "Responses of cerebral arterioles to adenosine 5'–diphosphate, serotonin, and the thromboxane analogue U–46619 during chronic hypertension," *Hypertension.* 1988 Dec.;12(6):556–61.

Mune, T. et al., "Human hypertension caused by mutations in the kidney isozyme of 11 beta–hydroxysteroid dehydrogenase," *Nat Genet.* 1995 Aug.;10(4):394–9.

Nara, Y. et al., "Blood pressure cosegregates with a microsatellite of angiotensin I converting enzyme (ACE) in F2 generation from a cross between original normotensive Wistar–Kyoto rat (WKY) and stroke–prone spontaneously hypertensive rat (SHRSP)," *Biochem Biophys Res Commun.* Dec. 31, 1991; 181(3):941–6.

Newcomb, P. et al., "Pericyte growth and contractile phenotype: modulation by endothelial–synthesized matrix and comparison with aortic smooth muscle," *J Cell Physiol.* 1993 May;155(2):385–93.

Oparil, S., "The sympathetic nervous system in clinical and experimental hypertension," *Kidney Int.* 1986 Sep.; 30(3):437–52.

Panza, J.A., "Endothelium–dependent vasodilatation and essential hypertension," *N Engl J Med.* Oct. 6 1994;331(14):951.

Panza, J.A. et al., "Effect of increased availability of endothelium–derived nitric oxide precursor on endothelium–dependent vascular relaxation in normal subjects and in patients with essential hypertension," *Circulation.* 1993 May;87(5):1475–81.

Panza, J.A. et al., "Abnormal endothelium–dependent vascular relaxation in patients with essential hypertension," *N Engl J Med.* Jul. 5, 1990;323(1):22–7.

Patek, C.E. et al., "A zinc finger truncation of murine WT1 results in the characteristic urogenital abnormalities of Denys–Drash syndrome," *PNAS.* Mar. 16, 1999;96(6):2931–6.

Peerless, S.J., "Risk factors of moyamoya disease in Canada and the USA," *Clin Neurol Neurosurg.* 1997 Oct;99 Suppl 2:S45–8.

Pelletier, J., "Molecular genetics of Wilms' tumor: insights into normal and abnormal renal development," *Can J Oncol.* 1994 Apr.;4(2):262–72.

Pesce, C.M. et al., "Glomerulosclerosis at both early and late stages is associated with increased cell turnover in mice transgenic for growth hormone," *Lab Invest.* 1991 Nov.;65(5):601–5.

Rapp, J.P. et al., "A genetic polymorphism in the renin gene of Dahl rats cosegregates with blood pressure," *Science.* Jan. 27, 1989;243(4890):542–4.

Samani, N.J. et al., "A gene differentially expressed in the kidney of the spontaneously hypertensive rat cosegregates with increased blood pressure," *J Clin Invest.* 1993 Aug.;92(2):1099–103.

Schober, M. et al., "An increased pool of secretory hormones and peptides in adrenal medulla of stroke–prone spontaneously hypertensive rats," *Hypertension.* 1989 May;13(5):469–74.

Schloekmann, H.O. et al., "TGF–beta1–induced cell cycle arrest in renal mesangial cells involves inhibition of cyclin E–cdk 2 activation and retinoblastoma protein phosphorylation," *Kidney Int.* 1997 Apr.;51(4):1228–36.

Shankland, S.J. et al., "Mesangial cell proliferation mediated by PDGF and bFGF is determined by levels of the cyclin kinase inhibitor p27Kip1," *Kidney Int.* 1997 Apr.;51(4):1088–99.

Shimkets, R.A. et al., "Liddle's syndrome: heritable human hypertension caused by mutations in the beta subunit of the epithelial sodium channel," *Cell.* Nov. 4, 1994;79(3):407–14.

Siegel, J.F. et al., "Unilateral nephrectomy induces the expression of the Wilms tumor gene in the contralateral kidney of the adult rat," *J. Urol.* 1996 Aug.;156(2 Pt 2):688–92.

Sterzel, R.B. et al., "Cytokines and mesangial cells," *Kidney Int Suppl.* 1993;39:S26–31.

StLezin, E. et al., "Hypertensive strains and normotensive 'control' strains. How closely are they related?" *Hypertension.* 1992 May;19(5):419–24.

Sturzl, M. et al., "Run–off" synthesis and application of defined single–stranded DNA hybridization probes, *Anal Biochem.* Feb. 15, 1990;185(1):164–9.

Taddei, S. et al., "Vasodilation to acetylcholine in primary and secondary forms of human hypertension," *Hypertension.* 1993 Jun.;21(6 Pt 2):929–33.

Takiyyuddin, M.A. et al., "Catecholamine secretory vesicles. Augmented chromogranins and amines in secondary hypertension," *Hypertension,* 1993 May;21(5):674–9.

Tamaki, K. et al., "Evidence that disruption of the blood–brain barrier precees reduction in cebral blood flow in hypertensive encephalopathy," *Hypertension,* 6:175–81 (1984).

Tamaki, K. et al., "Increased susceptibility to osmotic disruption of the blood–brain barrier in chronic hypertension," *Hypertension.* 1984 Sep.–Oct.;6(5):633–8.

Tommerup, N. et al., "Isolation and fine mapping of 16 novel human zinc finger–encoding cDNAs identify putative candidate genes for developmental and malignant disorders," *Genomics.* May 20, 1995;27(2):259–64.

Tschudi, M.R. et al., "Characterization of contractile endothelin and angiotensin receptors in human resistance arteries: evidence for two endothelin and one angiotensin receptor," *Biochem Biophys Res Commun.* Oct. 28, 1994;204(2):685–90.

Vortkamp, A. et al., "GLI3 zinc–finger gene interrupted by translocations in Greig syndrome families," *Nature.* Aug. 8, 1991;352(6335):539–40.

Webb, R.C. et al., "Increased–vasodilator responses to acetylcholine in psychosocial hypertensive mice," *Hypertension.* 1987 Mar.;9(3):268–76.

Witzgall, R. et al., "Kid–1, a putative renal transcription factor: regulation during ontogeny and in response to ischemia and toxic injury," *Mol Cell Biol.* 1993 Mar.;13(3):1933–42.

Wright, C.E. et al., "Effects of hypertension and hypercholesterolemia on vasodilatation in the rabbit," *Hypertension.* 1986 May;8(5):361–71.

Yamori, Y., Physiopathology of the various strains of spontaneously hypertensive rats. In Hypertension. J. Genest. O. Kuchel, P. Hamet, and M. Cantin, editors. McGraw–Hill, New York, NY 556–81 (1982).

Yang, S.T. et al., "Mechanisms of impaired endothelium–dependent cerebral vasodilation in response to bradykinin in hypertensive rats," *Stroke,* 22:1172–82 (1991).

Genbank Accession No. AA172526 for ms96d09.r1 Soares mouse 3NbMS Mus musculus cDNA clone IMAGE: 619409 5' similar to SW:ZN91_HUMAN Q05481 ZINC FINGER PROTEIN 91;, mRNA sequence.

Genbank Accession No. AA159831 for zo56d04.r1 Stratagene pancreas (#937208) Homo sapiens cDNA clone IMAGE:590887 5' similar to contains element L1 repetitive element;, mRNA sequence.

Genbank Accession No. AA612258 for vo04e12.r1 Stratagene mouse skin (#937313) Mus musculus cDNA clone IMAGE:1040494 5' similar to TR:G1256362 G1256362 ZINC FINGER PROTEIN. ;, mRNA sequence.

Genbank Accession No. AA99050 for vn40e05.r1 Stratagene mouse skin (#937313) Mus musculus cDNA clone IMAGE:1023680 5' similar to gb:X07290_cds1 ZINC FINGER PROTEIN HF.12 (HUMAN); gb:M36146 Mouse zinc finger (MOUSE);, mRNA sequence.

Genbank Accession No. AA103332 for mo24d04.r1 Life Tech mouse embryo 13 5dpc 10666014 Mus musculus cDNA clone 554503 5'.

```
xLYQCSGCGKTFASRSSYIIHMKRKRHAIKIKPES
GSLPFSQDTAFAIPQSGHNTEEPNQCKYCGRAFH
NRSFLLIHERIHTREKPYKCRECEKACRWRSNLY
RHERKHFLHKRRKYHESKETSNLQSKIFIDEKPF
WCQECGKTFTRKRSLLDHKGIHSGERRFKCNLC
EKSFDRNYRLVNKQRIHTTEQPFQSQWHDKDFA
GTHAHSVDQRKHRTLQSEYSLQSDKPGLSYCQD
VRVNIQELELSGKKPLDNxTSNLQSKIFIDEKPFW
CQECGKTFTRKRSLLDHKGIHSGERRFKCNLCE
KSFDRNYRVLLITRGSTLQSNHFNLSGMIKTLLG
HMPILLIRESTEHCSLNIxDEKPFCQECGKTFTRK
RSLLDHKGIHSGERRFKCNLCEKSFDRNYRVLLI
TRGSTLQS
```

Fig. 3

| cell type | Number of positive nuclei | Percentage of positive nuclei |
|---|---|---|
| SHR | 165/200 | 82.5% |
| WKY | 77/200 | 38.5% |

```
1    TGCTGACAGAGTCCTGGGATAACCTAGGGGCCAGGGCCTCTATCAGACCC    50
     ||||||||||||||||||||||||||||||||||||||||||||||||||
1    TGCTGACAGAGTCCTGGGATAACCTAGGGGCCAGGGCCTCTATCAGACCC    50

51   CAGAGAACGTTCTGTTCTTTACCAACATCACTTTTCAGCAATAAGACTGA   100
     ||||||||||||||||||||||||||||||||||||||||||||||||||
51   CAGAGAACGTTCTGTTCTTTACCAACATCACTTTTCAGCAATAAGACTGA   100

101  GGAGTCTCTGAATTTTGAAACCATCAAGCTTCCACACCAAGAACATCCCA   150
     ||||||||||||||||||||||||||||||||||||||||||||||||||
101  GGAGTCTCTGAATTTTGAAACCATCAAGCTTCCACACCAAGAACATCCCA   150

151  GCCAGAAAGGCCTGGGCCTTTACAAAGGTTTCCCCAGTGCCTACCACTTA   200
     ||||||||||||||||||||||||||||||||||||||||||||||||||
151  GCCAGAAAGGCCTGGGCCTTTACAAAGGTTTCCCCAGTGCCTACCACTTA   200

201  AGTTCTCTAGAGATGTAATCAGGAACTACTCCCCACCCCACTGTCATCAA   250
     ||||||||||||||||||||||||||||||||||||||||||||||||||
201  AGTTCTCTAGAGATGTAATCAGGAACTACTCCCCACCCCACTGTCATCAA   250

251  AGACCCCAGGCTAATCTCTAAAATGGCTTTTCACATGCCTGGTCAAATTG   300
     ||||||||||||||||||||||||||||||||||||||||||||||||||
251  AGACCCCAGGCTAATCTCTAAAATGGCTTTTCACATGCCTGGTCAAATTG   300

301  GAAGACCACCCGA.....................................   350
     |||||||||||||
301  GAAGACCACCCGA.....................................   350
```

Fig. 11A

```
  1    TCGGGTGGTCTTCCAATTTGAC-CAGGCATGTGAAAAGCCATTTTAGAGA    50
         ||||||||||||||||||||| | ||||| |||||| |||| ||||| |
  1    TCGGGTGGTCTTCCAATTTGACTC-GGCATATGAAAAACCATGTTAGAAA    50

51    TTAGCCTGGGGTCTTTGATGACAGTGGGG-TGGGGAGTAGTTCCTGATTA   100
         |||||||||||||| |||||||||||||| |||||| |||||||| || ||
 51    TTAGCCTGGGGTCTTCGATGACAGTGGGGGTGGGGAATAGTTCTTGGTCA   100

101    CATCTCTAGAGAACTTAAGTGGTAGGCACTGGGGAAA-CCTTTGTAAAGG   150
         ||| |||||||||||| |||||||||||||||||||| ||||||||||||
101    CAT-TCTAGAGAACTTTAGTGGTAGGCACTGGGGAAAACCTTTGTAAAGG   150

151    CCCAGGCCTTTCTGGCTGGGATGTTCTTGGTGTGGAAGCTTGATGGTTTC   200
         |||| |||||| ||||| ||||||||||||||||||| ||||||||||||
151    TCCAGTCCTTTTTGGCTTGGATGTTCTTGGTGTGGAATCTTGATGGTTTC   200

201    AAAATTCAGAGACTC-CTCAGTCTTA-TTGCTGAAAAGTGATGTTGGTAA   250
         |||| |||| || | ||||||||| || ||| |||||| ||
201    AAAACTCAG-GAATTTCTCAGTCTTCCTT-CTGGAAAGAGATGTTGAAAA   250

251    AGAACAGAACGTTCTCTGGGGTCTGATAGAGGCC-CTGGCCCCTAGGTT-   300
         | |||||||| |||||||||||||    ||| ||      ||||||||||||
251    ATAACAGAAAGTTCTCTGGGGTCTTTTAG-GGATTCTGGCCCCTAGGTTT   300

301    ATCCCAGGACTCTGTCAGCA..............................   350
         ||||||||||||||||||||
301    ATCCCAGGACTCTGTCAGC...............................   350
```

Fig. 11B

HATF-1 5' end amino acid sequence

```
L Y Q C S G C G K T F A S R S
S Y I I H M K R K R H A I K I
K P E S G S L P F S Q D T A F
A I P Q S G H N T E E P N Q C
K Y C G R A F H N R S F L L I
H E R I H T R E K P Y K C R E
C E K A C R W R S N L Y R H E
R K H F L H K R R K Y H E S K
E T S N L Q S K I F I D E K P
F W C Q E C G K T F T R K R S
L L D H K G I H S G E R R F K
C N L C E K S F D R N Y R L V
N H Q R I H T T E Q P F Q S Q
W H D K D F A G T H A H S V D
Q R K H R T L Q S E Y S L Q S
D K P G L S Y C Q D V R V N I
Q E L E L S G K K P L D N
```

HATF-1 5' end nucleic acid sequence

```
CAGAAACTGTACCAGTGTAGTGGGTGTGGGAAAACATTTGCCTCTAGGTC
CTCTTATATTATTCATATGAAGCGAAAGCGACATGCTATTAAAATAAAAC
CTGAAAGTGGCTCTCTACCTTTTAGTCAGGATACAGCATTTGCCATTCCTC
AGAGTGGTCATAATACAGAGGAGCCTAATCAGTGTAAATACTGTGGCAGA
GCCTTCCATAATCGCTCATTTCTTCTCATTCACGAGAGAATTCACACTAGA
GAGAAGCCCTATAAGTGCAGGGAGTGTGAAAAAGCTTGCCGATGGAGGT
CCAATCTCTACCGACATGAGAGAAAACACTTTTTGCACAAGCGGCGTAAG
TATCATGAAAGTAAAGAGACTTCAAATCTACAGTCAAAAATCTTCATTGA
TGAGAAGCCCTTTTGGTGTCAAGAATGTGGGAAAACCTTTACACGTAAAA
GAAGCCTTTTAGATCATAAGGGAATACACAGTGGAGAGAGACGCTTTAAG
TGCAACTTGTGTGAAAAATCTTTTGATAGAAACTACCGTCTTGTTAATCAC
CAGAGGATCCACACTACAGAGCAACCATTTCAATCTCAGTGGCATGATAA
AGACTTTGCTGGGACACATGCCCATTCTGTTGATCAGAGAAAACACAGAA
CACTGCAGTCTGAATATAGCCTACAATCAGATAAGCCTGGCTTATCCTACT
GTCAGGATGTAAGGGTAAATATTCAGAATTAGAACTAAGTGGAAAGAAG
CCCCTTGATAACCCTTCTCATGAGAGTTCCATGTCCACCGGCATTCC
```

Fig. 12

HATF-1 3' end amino acid sequence

```
A D R V R D N L G A R A S I R
P D R T F C S L P T S L F S N
K T E E S L N F E P S S F H T
K N I Q P E R P G P L Q R F P
Q C L P L K F S R D V I R N Y
S P P H C H Q R P Q A N L *
```

HATF-1 3' end nucleic acid sequence
(identical between rat, human and mouse)

```
TGCTGACAGAGTCCGGGATAACCTAGGGGCCAGGGCCTCTATCAGACCCG
ACAGAACGTTCTGTTCTTTACCAACATCACTTTTCAGCAATAAGACTGAGG
AGTCTCTGAATTTTGAACCATCAAGCTTCCACACCAAGAACATCCAGCCA
GAAAGGCCTGGGCCTTTACAAAGGTTTCCCCAGTGCCTACCACTTAAGTTC
TCTAGAGATGTAATCAGGAACTACTCCCCACCCCACTGTCATCAAAGACC
CCAGGCTAATCTCTAAAATGGCTTTTCACATGCCTGGTCAAATTGGAAGAC
CACCCGA
```

Fig. 13

HRP-1 nucleic acid sequence

```
TCGGGTGGTCTTCCAATTTGACTCGGCATATGAAAAACCATGTTAGAAATT
AGCCTGGGGTCTTCGATGACAGTGGGGGTGGGGAATAGTTCTTGGTCACA
TTCTAGAGAACTTTAGTGGTAGGCACTGGGGAAAACCTTTGTAAAGGTCC
AGTCCTTTTTGGCTTGGATGTTCTTGGTGTGGAATCTTGATGGTTTCAAAA
CTCAGGAATTTCTCAGTCTTCCTTCTGGAAAGAGATGTTGAAAAATAACA
GAAAGTTCTCTGGGGTCTTTTAGGGATTCTGGCCCCTAGGTTTATCCCAGG
ACTCTGTCAGC
```

Fig. 14

SEQUENCE LISTING

<160> NUMBER OF SEQ ID NOS: 19

<210> SEQ ID NO 1
<211> LENGTH: 800
<212> TYPE: DNA
<213> ORGANISM: Homo sapiens
<220> FEATURE:
<221> NAME/KEY: CDS
<222> LOCATION: (7)..(765)

<400> SEQUENCE: 1

```
cagaaa ctg tac cag tgt agt ggg tgt ggg aaa aca ttt gcc tct agg        48
       Leu Tyr Gln Cys Ser Gly Cys Gly Lys Thr Phe Ala Ser Arg
         1               5                  10 tcc tct tat att att cat atg aag cga aag cga cat gct att aaa ata        96
Ser Ser Tyr Ile Ile His Met Lys Arg Lys Arg His Ala Ile Lys Ile
 15                  20                  25                  30 aaa cct gaa agt ggc tct cta cct ttt agt cag gat aca gca ttt gcc       144
Lys Pro Glu Ser Gly Ser Leu Pro Phe Ser Gln Asp Thr Ala Phe Ala
                 35                  40                  45 att cct cag agt ggt cat aat aca gag gag cct aat cag tgt aaa tac       192
```

```
Ile Pro Gln Ser Gly His Asn Thr Glu Glu Pro Asn Gln Cys Lys Tyr
            50                  55                  60 tgt ggc aga gcc ttc cat aat cgc tca ttt ctt ctc att cac gag aga      240
Cys Gly Arg Ala Phe His Asn Arg Ser Phe Leu Leu Ile His Glu Arg
         65                  70                  75 att cac act aga gag aag ccc tat aag tgc agg gag tgt gaa aaa gct      288
Ile His Thr Arg Glu Lys Pro Tyr Lys Cys Arg Glu Cys Glu Lys Ala
     80                  85                  90 tgc cga tgg agg tcc aat ctc tac cga cat gag aga aaa cac ttt ttg      336
Cys Arg Trp Arg Ser Asn Leu Tyr Arg His Glu Arg Lys His Phe Leu
 95                 100                 105                 110 cac aag cgg cgt aag tat cat gaa agt aaa gag act tca aat cta cag      384
His Lys Arg Arg Lys Tyr His Glu Ser Lys Glu Thr Ser Asn Leu Gln
                115                 120                 125 tca aaa atc ttc att gat gag aag ccc ttt tgg tgt caa gaa tgt ggg      432
Ser Lys Ile Phe Ile Asp Glu Lys Pro Phe Trp Cys Gln Glu Cys Gly
            130                 135                 140 aaa acc ttt aca cgt aaa aga agc ctt tta gat cat aag gga ata cac      480
Lys Thr Phe Thr Arg Lys Arg Ser Leu Leu Asp His Lys Gly Ile His
        145                 150                 155 agt gga gag aga cgc ttt aag tgc aac ttg tgt gaa aaa tct ttt gat      528
Ser Gly Glu Arg Arg Phe Lys Cys Asn Leu Cys Glu Lys Ser Phe Asp
    160                 165                 170 aga aac tac cgt ctt gtt aat cac cag agg atc cac act aca gag caa      576
Arg Asn Tyr Arg Leu Val Asn His Gln Arg Ile His Thr Thr Glu Gln
175                 180                 185                 190 cca ttt caa tct cag tgg cat gat aaa gac ttt gct ggg aca cat gcc      624
Pro Phe Gln Ser Gln Trp His Asp Lys Asp Phe Ala Gly Thr His Ala
                195                 200                 205 cat tct gtt gat cag aga aaa cac aga aca ctg cag tct gaa tat agc      672
His Ser Val Asp Gln Arg Lys His Arg Thr Leu Gln Ser Glu Tyr Ser
            210                 215                 220 cta caa tca gat aag cct ggc tta tcc tac tgt cag gat gta agg gta      720
Leu Gln Ser Asp Lys Pro Gly Leu Ser Tyr Cys Gln Asp Val Arg Val
        225                 230                 235 aat att cag gaa tta gaa cta agt gga aag aag ccc ctt gat aac          765
Asn Ile Gln Glu Leu Glu Leu Ser Gly Lys Lys Pro Leu Asp Asn
    240                 245                 250 ccttctcatg agagttccat gtccaccggc attcc                               800

<210> SEQ ID NO 2
<211> LENGTH: 253
<212> TYPE: PRT
<213> ORGANISM: Homo sapiens

<400> SEQUENCE: 2

Leu Tyr Gln Cys Ser Gly Cys Gly Lys Thr Phe Ala Ser Arg Ser Ser
 1               5                  10                  15

Tyr Ile Ile His Met Lys Arg Lys Arg His Ala Ile Lys Ile Lys Pro
            20                  25                  30

Glu Ser Gly Ser Leu Pro Phe Ser Gln Asp Thr Ala Phe Ala Ile Pro
         35                 40                  45

Gln Ser Gly His Asn Thr Glu Glu Pro Asn Gln Cys Lys Tyr Cys Gly
     50                  55                  60

Arg Ala Phe His Asn Arg Ser Phe Leu Leu Ile His Glu Arg Ile His
 65                 70                  75                  80

Thr Arg Glu Lys Pro Tyr Lys Cys Arg Glu Cys Glu Lys Ala Cys Arg
             85                  90                  95
```

```
Trp Arg Ser Asn Leu Tyr Arg His Glu Arg Lys His Phe Leu His Lys
            100                 105                 110
Arg Arg Lys Tyr His Glu Ser Lys Glu Thr Ser Asn Leu Gln Ser Lys
        115                 120                 125
Ile Phe Ile Asp Glu Lys Pro Phe Trp Cys Gln Cys Gly Lys Thr
    130                 135                 140
Phe Thr Arg Lys Arg Ser Leu Leu Asp His Lys Gly Ile His Ser Gly
145                 150                 155                 160
Glu Arg Arg Phe Lys Cys Asn Leu Cys Glu Lys Ser Phe Asp Arg Asn
                165                 170                 175
Tyr Arg Leu Val Asn His Gln Arg Ile His Thr Thr Glu Gln Pro Phe
            180                 185                 190
Gln Ser Gln Trp His Asp Lys Asp Phe Ala Gly Thr His Ala His Ser
        195                 200                 205
Val Asp Gln Arg Lys His Arg Thr Leu Gln Ser Glu Tyr Ser Leu Gln
    210                 215                 220
Ser Asp Lys Pro Gly Leu Ser Tyr Cys Gln Asp Val Arg Val Asn Ile
225                 230                 235                 240
Gln Glu Leu Glu Leu Ser Gly Lys Lys Pro Leu Asp Asn
                245                 250
```

<210> SEQ ID NO 3
<211> LENGTH: 310
<212> TYPE: DNA
<213> ORGANISM: Homo sapiens
<220> FEATURE:
<221> NAME/KEY: CDS
<222> LOCATION: (2)..(265)

<400> SEQUENCE: 3

```
t gct gac aga gtc cgg gat aac cta ggg gcc agg gcc tct atc aga ccc       49
  Ala Asp Arg Val Arg Asp Asn Leu Gly Ala Arg Ala Ser Ile Arg Pro
   1               5                  10                  15
gac aga acg ttc tgt tct tta cca aca tca ctt ttc agc aat aag act        97
Asp Arg Thr Phe Cys Ser Leu Pro Thr Ser Leu Phe Ser Asn Lys Thr
            20                  25                  30
gag gag tct ctg aat ttt gaa cca tca agc ttc cac acc aag aac atc       145
Glu Glu Ser Leu Asn Phe Glu Pro Ser Ser Phe His Thr Lys Asn Ile
        35                  40                  45
cag cca gaa agg cct ggg cct tta caa agg ttt ccc cag tgc cta cca       193
Gln Pro Glu Arg Pro Gly Pro Leu Gln Arg Phe Pro Gln Cys Leu Pro
    50                  55                  60
ctt aag ttc tct aga gat gta atc agg aac tac tcc cca ccc cac tgt       241
Leu Lys Phe Ser Arg Asp Val Ile Arg Asn Tyr Ser Pro Pro His Cys
65                  70                  75                  80
cat caa aga ccc cag gct aat ctc taaaatggct tttcacatgc ctggtcaaat      295
His Gln Arg Pro Gln Ala Asn Leu
                85
tggaagacca cccga                                                      310
```

<210> SEQ ID NO 4
<211> LENGTH: 88
<212> TYPE: PRT
<213> ORGANISM: Homo sapiens

<400> SEQUENCE: 4

```
Ala Asp Arg Val Arg Asp Asn Leu Gly Ala Arg Ala Ser Ile Arg Pro
 1               5                  10                  15
Asp Arg Thr Phe Cys Ser Leu Pro Thr Ser Leu Phe Ser Asn Lys Thr
```

```
                20                  25                  30
Glu Glu Ser Leu Asn Phe Glu Pro Ser Ser Phe His Thr Lys Asn Ile
             35                  40                  45

Gln Pro Glu Arg Pro Gly Pro Leu Gln Arg Phe Pro Gln Cys Leu Pro
         50                  55                  60

Leu Lys Phe Ser Arg Asp Val Ile Arg Asn Tyr Ser Pro Pro His Cys
 65                  70                  75                  80

His Gln Arg Pro Gln Ala Asn Leu
                 85

<210> SEQ ID NO 5
<211> LENGTH: 314
<212> TYPE: DNA
<213> ORGANISM: Murine sp.

<400> SEQUENCE: 5
tcgggtggtc ttccaatttg actcggcata tgaaaaacca tgttagaaat tagcctgggg      60
tcttcgatga cagtgggggt ggggaatagt tcttggtcac attctagaga acttagtgg     120 taggcactgg ggaaaacctt tgtaaaggtc cagtcctttt tggcttggat gttcttggtg    180
tggaatcttg atggtttcaa aactcaggaa tttctcagtc ttccttctgg aaagagatgt    240
tgaaaaataa cagaaagttc tctggggtct tttagggatt ctggccccta ggtttatccc    300
aggactctgt cagc                                                      314

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 6
aagtgctgca tttgtggcag                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 7
gcttcttagt gggcacattc                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 8
gaatgccggt ggacatggaa                                                 20

<210> SEQ ID NO 9
<211> LENGTH: 21
<212> TYPE: DNA
<213> ORGANISM: Artificial Sequence
<220> FEATURE:
```

```
<223> OTHER INFORMATION: Description of Artificial Sequence: synthetic
      primer

<400> SEQUENCE: 9
gtcttcttga catctctctt g                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 10
ttacggacct ctttgccatg                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 11
gtaaagtttg acttccaccg                                                20

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: synthetic
      primer

<400> SEQUENCE: 12

Glu Leu Ser Gly Lys Lys Pro Leu Asp Asn Pro Ser His Glu Ser Ser
  1               5                  10                  15

Met

<210> SEQ ID NO 13
<211> LENGTH: 41
<212> TYPE: PRT
<213> ORGANISM: Artificial Sequence
<220> FEATURE:
<223> OTHER INFORMATION: Description of Artificial Sequence: synthetic
      primer

<400> SEQUENCE: 13

Glu Lys Pro Phe Trp Cys Gln Glu Cys Gly Lys Thr Phe Thr Arg Lys
  1               5                  10                  15

Arg Ser Leu Leu Asp His Lys Gly Ile His Ser Gly Leu Arg Arg Phe
                 20                  25                  30

Lys Cys Asn Leu Cys Glu Lys Ser Phe
             35                  40

<210> SEQ ID NO 14
<211> LENGTH: 43
<212> TYPE: PRT
<213> ORGANISM: Artificial Sequence
<220> FEATURE:
<223> OTHER INFORMATION: Description of Artificial Sequence: synthetic
      primer

<400> SEQUENCE: 14
```

Val Lys Pro Phe Gln Cys Lys Thr Cys Gln Arg Lys Phe Ser Arg Ser
1               5                   10                  15

Asp His Leu Lys Thr His Thr Arg Thr His Thr Gly Glu Lys Pro Phe
                20                  25                  30

Ser Cys Arg Trp Pro Ser Cys Gln Lys Lys Phe
            35                  40

<210> SEQ ID NO 15
<211> LENGTH: 41
<212> TYPE: PRT
<213> ORGANISM: Artificial Sequence
<220> FEATURE:
<223> OTHER INFORMATION: Description of Artificial Sequence: synthetic
      primer

<400> SEQUENCE: 15

Glu Lys Pro Tyr Gln Cys Ser Leu Cys Gly Lys Ala Phe Gln Arg Ser
1               5                   10                  15

Ser Ser Leu Val Gln His Gln Arg Ile His Thr Gly Glu Lys Pro Tyr
                20                  25                  30

Arg Cys Asn Leu Cys Gly Arg Ser Phe
            35                  40

<210> SEQ ID NO 16
<211> LENGTH: 41
<212> TYPE: PRT
<213> ORGANISM: Artificial Sequence
<220> FEATURE:
<223> OTHER INFORMATION: Description of Artificial Sequence: synthetic
      primer

<400> SEQUENCE: 16

Glu Lys Cys Tyr Glu Cys Asn Glu Cys Gly Lys Thr Phe Thr Arg Ser
1               5                   10                  15

Ser Asn Leu Ile Val His Gln Arg Ile His Thr Gly Glu Lys Pro Phe
                20                  25                  30

Ala Cys Asn Asp Cys Gly Lys Ala Phe
            35                  40

<210> SEQ ID NO 17
<211> LENGTH: 40
<212> TYPE: PRT
<213> ORGANISM: Artificial Sequence
<220> FEATURE:
<223> OTHER INFORMATION: Description of Artificial Sequence: synthetic
      primer

<400> SEQUENCE: 17

Glu Lys Pro Tyr Val Cys Lys Glu Cys Gly Lys Ala Phe Thr Leu Ser
1               5                   10                  15

Thr Ser Leu Tyr Lys His Leu Arg Thr His Thr Val Glu Lys Ser Tyr
                20                  25                  30

Arg Cys Lys Glu Cys Gly Lys Ser
            35                  40

<210> SEQ ID NO 18
<211> LENGTH: 45
<212> TYPE: PRT
<213> ORGANISM: Artificial Sequence
<220> FEATURE:
<223> OTHER INFORMATION: Description of Artificial Sequence: synthetic
      primer -continued

```
<400> SEQUENCE: 18

Glu Lys Pro Phe Gln Cys Thr Phe Glu Gly Cys Gly Lys Arg Phe Ser
 1               5                  10                  15

Leu Asp Phe Asn Leu Arg Thr His Val Arg Ile His Thr Gly Asp Arg
             20                  25                  30

Pro Tyr Val Cys Pro Phe Asp Gly Cys Asn Lys Lys Phe
         35                  40                  45

<210> SEQ ID NO 19
<211> LENGTH: 23
<212> TYPE: PRT
<213> ORGANISM: Artificial Sequence
<220> FEATURE:
<223> OTHER INFORMATION: Any 2 amino acids at postitions 2-5 may be
      absent-intended to equal a range of 2-4 amino acids
<220> FEATURE:
<223> OTHER INFORMATION: Any 2 amino acids at positions 7-9 may be
      absent-intended to equal a range of 1-3 amino acids
<220> FEATURE:
<223> OTHER INFORMATION: Xaa's at positions 11-15, 17,18, and 20-22
      may be any amino acid
<220> FEATURE:
<223> OTHER INFORMATION: Description of Artificial Sequence: synthetic
      primer

<400> SEQUENCE: 19

Cys Xaa Xaa Xaa Xaa Cys Xaa Xaa Xaa Phe Xaa Xaa Xaa Xaa Xaa Leu
 1               5                  10                  15

Xaa Xaa His Xaa Xaa Xaa His
             20
```

HYPERTENSION ASSOCIATED TRANSCRIPTION FACTORS AND USES THEREFOR

RELATED APPLICATIONS

This application claims priority to U.S. provisional Application No. 60/099,289, filed on Sep. 4, 1998, incorporated herein in its entirety by this reference.

BACKGROUND OF THE INVENTION

Hypertension is a multi-factorial, pathogenic process associated with a number of occlusive vascular diseases including myocardial infarction, stroke, and end-stage renal failure (Lifton, R. P. (1995) *Proc. Nat. Acad. Sci.* 92:8545–51). Essential (or primary) human hypertension, as opposed to the more rare monogenetic forms, appears to be controlled by genetic and epigenetic events. To date, several forms of monogenetic (Mendelian) human hypertension have been reported, where single gene defects result in a hypertensive phenotype in the vast majority of affected individuals. These include pseudoaldosteronism (Liddle syndrome, described in Shimkets, R. A. et al. (1994) *Cell* 79:407–14), glucocorticoid-remediable aldosteronism (GRA, described in Lifton, et al. (1992) *Nature*. 355:262–5), and most recently apparent mineralocorticoid excess (AME, described in Mune et al. (1995) *Nat. Gen.* 10(4):394–9), and pseudohypoaldosteronism type II (Gordon syndrome, described in Gordon et al. (1995) Raven, N.Y., pp. 2111–23).

Evidence which supports the influence of heredity in essential hypertension includes epidemiologic studies, which demonstrate significant familial aggregation of blood pressure (Longini, et al. (1984) *Am. J. Epidemiol.* 120:131–44.) This is attributable to a genetic causation in that biological siblings have a higher level of blood pressure concordance than adoptive siblings raised within the same family (Biron et al. (1976) *Can. Med. Assoc. J.* 114:773–4). Additionally, identical twin studies have demonstrated a higher concordance in blood pressure than that seen in fraternal twins (Christian, J. C. (1985) Ross Laboratories, Columbus, Ohio, pp. 51–55). However, in spite of these observations a number of epigenetic factors have also been reasoned to influence development of hypertension, including age, body mass, gender, and diet (Lifton, R. P, 1995).

Investigations into the etiology and inception of human hypertension have been centered around the use of inbred animal models of genetic hypertension, which present efficient, easily manipulatable systems for molecular and genetic analyses. Rodent models of hypertension include the spontaneously hypertensive rat (SHR), the stroke-prone SHR (SP-SHR), the Dahl salt-sensitive rat, the John Rapp salt-sensitive strain of rat, and numerous mouse strains (Dzau et al. (1995) *Circulation* 92(2):521–31). Advantages of using rodent models of hypertension include the genetic homogeneity achieved by fully inbred strains and the ability to produce cross-bred hybrid strains of predetermined genetic composition in suitably large populations (Hubner et al. (1995) *Herz*. 20:309–14).

The widely-used SHR has been studied in great detail. This animal model is characterized by a number of phenotypic abnormalities, including vascular and cardiac hypertrophy, and alterations in angiotensin responsiveness, which have been linked to the development and maintenance of hypertension (Yamori, Y. (1982) *Hypertension*. pp-556–81). Changes in the SHR cerebral microcirculation have also been reported (Herman, I. M. et al, (1988). *Tissue & Cell*. 20(1):1–12. The SHR is amenable for mapping of genes linked to hypertension due to its genetic homogeneity. To date, candidate loci include angiotensin-converting enzyme (Jacob et al. (1991) *Cell*. 67:213–24), neuropeptide Y (NYP) (Katsuya et al (1993) *Biochem. Biophys. Res. Commun.* 192:261–7), renin (Rapp et al (1989) *Science*. 243:542–4), guanylyl cyclase A/atrial natriuretic peptide receptor (GCA) (Krieger et al (1994) *Hypertension* 12:(S3):S66), heat shock protein 70 (hsp70) (Hamet et al (1992) *Hypertension* 19:611–4); and $S_A$ (Krieger et al. (1992) *Hypertension* 20:412). The results of these studies confirm that like essential hypertension in humans, hypertension in rodents is a polygenic disease. This reinforces the importance of animal modeling in trying to understand human disease to determine the molecular mechanism(s) by which the onset of hypertension occurs and how the process is maintained.

SUMMARY OF THE INVENTION

The present invention is based, at least in part, on the discovery of novel molecules which are differentially expressed in hypertensive humans, rats, and mice, referred to herein as "hypertension associated transcription factor-1" ("HATF-1") nucleic acid and protein molecules, as well as homologues thereof, referred to herein as "HATF-1 Related Protein-1" ("HRP-1") nucleic acid and protein molecules. The HATF-1 and HRP-1 molecules of the present invention are useful as agents for diagnosing or prognosing subjects at risk for developing a cardiovascular disorder, e.g., hypertension, as well as modulating agents in regulating a variety of cellular processes. Accordingly, in one aspect, this invention provides isolated nucleic acid molecules encoding HATF-1 and HRP-1 proteins or biologically active portions thereof, as well as nucleic acid fragments suitable as primers or hybridization probes for the detection of HATF-1- encoding and HRP-1-encoding nucleic acids.

In one embodiment, an HATF-1 and HRP-1 nucleic acid molecule of the invention is at least 50%, 55%, 60%, 65%, 70%, 73%, 75%, 80%, 85%, 86%, 87%, 89%, 90%, 95%, 98%, or more homologous to the nucleotide sequence (e.g., to the entire length of the nucleotide sequence) shown in SEQ ID NO:1, 3, or 5 or a complement thereof.

In a preferred embodiment, the isolated nucleic acid molecule includes the nucleotide sequence shown SEQ ID NO:1, 3, or 5 or a complement thereof. In another preferred embodiment, the nucleic acid molecule consists of the nucleotide sequence shown in SEQ ID NO:1, 3, or 5. In another preferred embodiment, the nucleic acid molecule includes a fragment of at least 100 nucleotides of the nucleotide sequence of SEQ ID NO:1, 3, or 5 or a complement thereof.

Another embodiment of the invention features nucleic acid molecules, preferably HATF-1 and HRP-1 nucleic acid molecules, which specifically detect HATF-1 and HRP-1 nucleic acid molecules relative to nucleic acid molecules encoding non-HATF-1 and non-HRP-1 proteins, respectively. For example, in one embodiment, such a nucleic acid molecule is at least 20, 30, 40, 50, 60, 70, 80, 90, 100, 200–250, 250–300, 300–350, 350–400, 400–450, 450–500 or more nucleotides in length and hybridizes under stringent conditions to a nucleic acid molecule comprising the nucleotide sequence shown in SEQ ID NO:1, 3, or 5 or a complement thereof. In preferred embodiments, the nucleic acid molecules are at least 15 (e.g., contiguous) nucleotides in length and hybridize under stringent conditions to the nucleotide sequence of SEQ ID NO:1, 3, or 5 or a complement thereof.

Another embodiment of the invention provides an isolated nucleic acid molecule which is antisense to an HATF-1 or HRP-1 nucleic acid molecule, e.g., the coding strand of an HATF-1 or HRP-1 nucleic acid molecule.

Another aspect of the invention provides a vector comprising an HATF-1 or HRP-1 nucleic acid molecule. In certain embodiments, the vector is a recombinant expression vector. In another embodiment, the invention provides a host cell containing a vector of the invention.

In another aspect, the present invention provides a method for detecting the presence of an HATF-1 or HRP-1 nucleic acid molecule, protein or polypeptide in a biological sample by contacting the biological sample with an agent capable of detecting an HATF-1 or HRP-1 nucleic acid molecule, protein or polypeptide such that the presence of an HATF-1 or HRP-1 nucleic acid molecule, protein or polypeptide is detected in the biological sample.

In another aspect, the present invention provides a method for detecting the presence of HATF-1 or HRP-1 activity in a biological sample by contacting the biological sample with an agent capable of detecting an indicator of HATF-1 or HRP-1 activity such that the presence of HATF-1 or HRP-1 activity is detected in the biological sample.

In another aspect, the invention provides a method for modulating HATF-1 or HRP-1 activity comprising contacting a cell capable of expressing HATF-1 or HRP-1 with an agent that modulates HATF-1 or HRP-1 activity such that HATF-1 or HRP-1 activity in the cell is modulated. In one embodiment, the agent inhibits HATF-1 or HRP-1 activity. In another embodiment, the agent stimulates HATF-1 or HRP-1 activity. In one embodiment, the agent is an antibody that specifically binds to an HATF-1 or HRP-1 protein. In another embodiment, the agent modulates expression of HATF-1 or HRP-1 by modulating transcription of an HATF-1 or HRP-1 gene or translation of an HATF-1 or HRP-1 mRNA. In yet another embodiment, the agent is a nucleic acid molecule having a nucleotide sequence that is antisense to the coding strand of an HATF-1 or HRP-1 mRNA or an HATF-1 or HRP-1 gene.

In one embodiment, the methods of the present invention are used to treat a subject having a disorder characterized by aberrant HATF-1 or HRP-1 protein or nucleic acid expression or activity by administering an agent which is an HATF-1 or HRP-1 modulator to the subject. In one embodiment the HATF-1 and HRP-1 modulator is an HATF-1 or HRP-1 nucleic acid molecule. In another embodiment, the HATF-1 or HRP-1 modulator is an HATF-1 or HRP-1 protein. In yet another embodiment, the HATF-1 or HRP-1 modulator is a peptide, peptidomimetic, or other small molecule. In a preferred embodiment, the disorder characterized by aberrant HATF-1 or HRP-1 protein or nucleic acid expression is a cardiovascular disorder, e.g., hypertension.

The present invention also provides a diagnostic assay for identifying the presence or absence of a genetic alteration characterized by at least one of (i) aberrant modification or mutation of a gene encoding an HATF-1 or HRP-1 protein; (ii) mis-regulation of the gene; and (iii) aberrant post-translational modification of an HATF-1 or HRP-1 protein, wherein a wild-type form of the gene encodes an protein with an HATF-1 or HRP-1 activity.

In another embodiment, the invention features an isolated protein, preferably an HATF-1 or HRP-1 protein, which is encoded by a nucleic acid molecule having a nucleotide sequence at least about 50%, 55%, 60%, 65%, 70%, 73%, 75%, 80%, 85%, 86%, 87%, 89%, 90%, 95%, 98% or more homologous to a nucleotide sequence of SEQ ID NO:1, 3, 5 or a complement thereof. This invention further features an isolated protein, preferably an HATF-1 or HRP-1 protein, which is encoded by a nucleic acid molecule having a nucleotide sequence which hybridizes under stringent hybridization conditions to a nucleic acid molecule comprising the nucleotide sequence of SEQ ID NO:1, 3, 5, or a complement thereof.

The proteins of the present invention or biologically active portions thereof, can be operatively linked to a non-HATF-1 or a non-HRP-1 polypeptide (e.g., heterologous amino acid sequences) to form fusion proteins. The invention further features antibodies, such as monoclonal or polyclonal antibodies, that specifically bind proteins of the invention, preferably HATF-1 and HRP-1 proteins. In addition, the HATF-1 and HRP-1 proteins or biologically active portions thereof can be incorporated into pharmaceutical compositions, which optionally include pharmaceutically acceptable carriers.

In another embodiment, an HATF-1 and HRP-1 nucleic acid molecule includes a nucleotide sequence encoding a protein having an amino acid sequence sufficiently homologous to the amino acid sequence of SEQ ID NO:2 or 4. In a preferred embodiment, an HATF-1 and HRP-1 nucleic acid molecule includes a nucleotide sequence encoding a protein having an amino acid sequence at least 40%, 45%, 50%, 55%, 60%, 65%, 70%, 75%, 80%, 85%, 90%, 95% 98% or more homologous to the amino acid sequence of SEQ ID NO:2 or 4.

In another preferred embodiment, an isolated nucleic acid molecule encodes the amino acid sequence of human, rat, or mouse HATF-1 or HRP-1. In yet another preferred embodiment, the nucleic acid molecule includes a nucleotide sequence encoding a protein having the amino acid sequence of SEQ ID NO:2 or 4.

In other preferred embodiments, the nucleic acid molecule encodes a naturally occurring allelic variant of a polypeptide comprising the amino acid sequence of SEQ ID NO:2 or 4, wherein the nucleic acid molecule hybridizes to a nucleic acid molecule comprising SEQ ID NO: 1, 3, and/or 5 under stringent conditions.

Other features and advantages of the invention will be apparent from the following detailed description and claims.

BRIEF DESCRIPTION OF THE DRAWINGS

FIG. 3 depicts the deduced amino acid sequence of HATF-1 (human, rat, and mouse HATF-1 are 100% identical). The residues containing the seven zinc finger motifs are underlined. Discontinuities in the sequence are indicated by (x).

HATF-1 mRNA levels are 2- to 4-fold higher in neonatal SHR brains (lanes 1–3; 3, 5, or 9 days post-partum, respectively) than WKY (lanes 4–6: 3, 5, or 10 days post-partum, respectively). Equivalent RNA loading was confirmed by visualization of ethidium bromide-stained 28 and 18S bands.

Figure 5:
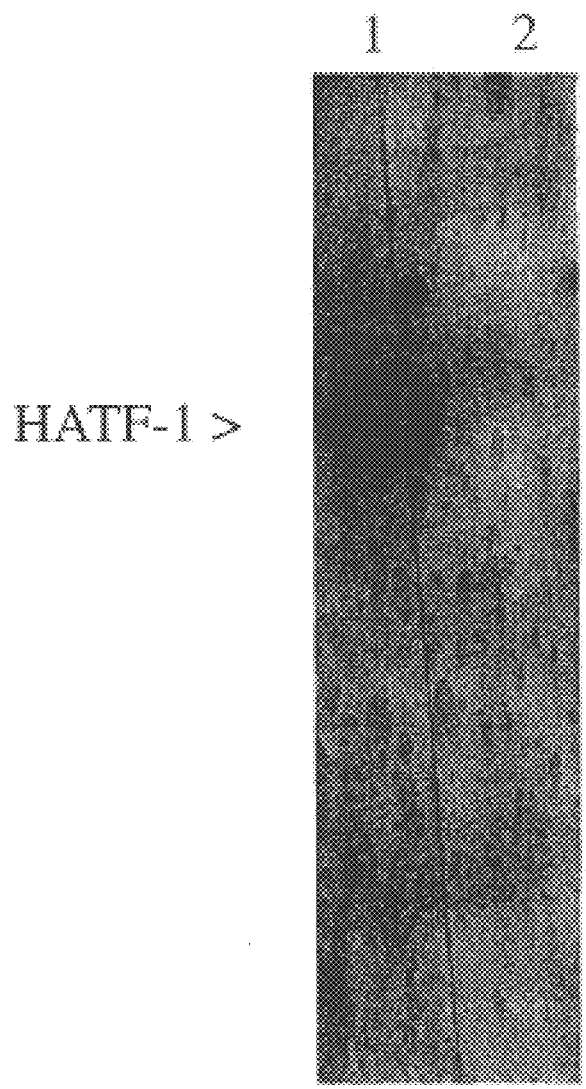

FIG. 5 is a gel depicting the differential expression of HATF-1 mRNA in cultured cerebrovascular endothelial cells of hypertensive rats. HATF-1 mRNA is strongly expressed in endothelial cells derived from SHR brains (lane 1) but is not detectable in endothelial cells derived from WKY brains (lane 2). Equivalent RNA loading was confirmed by visualization of ethidium bromide-stained 28 and 18S bands.

Figure 6:
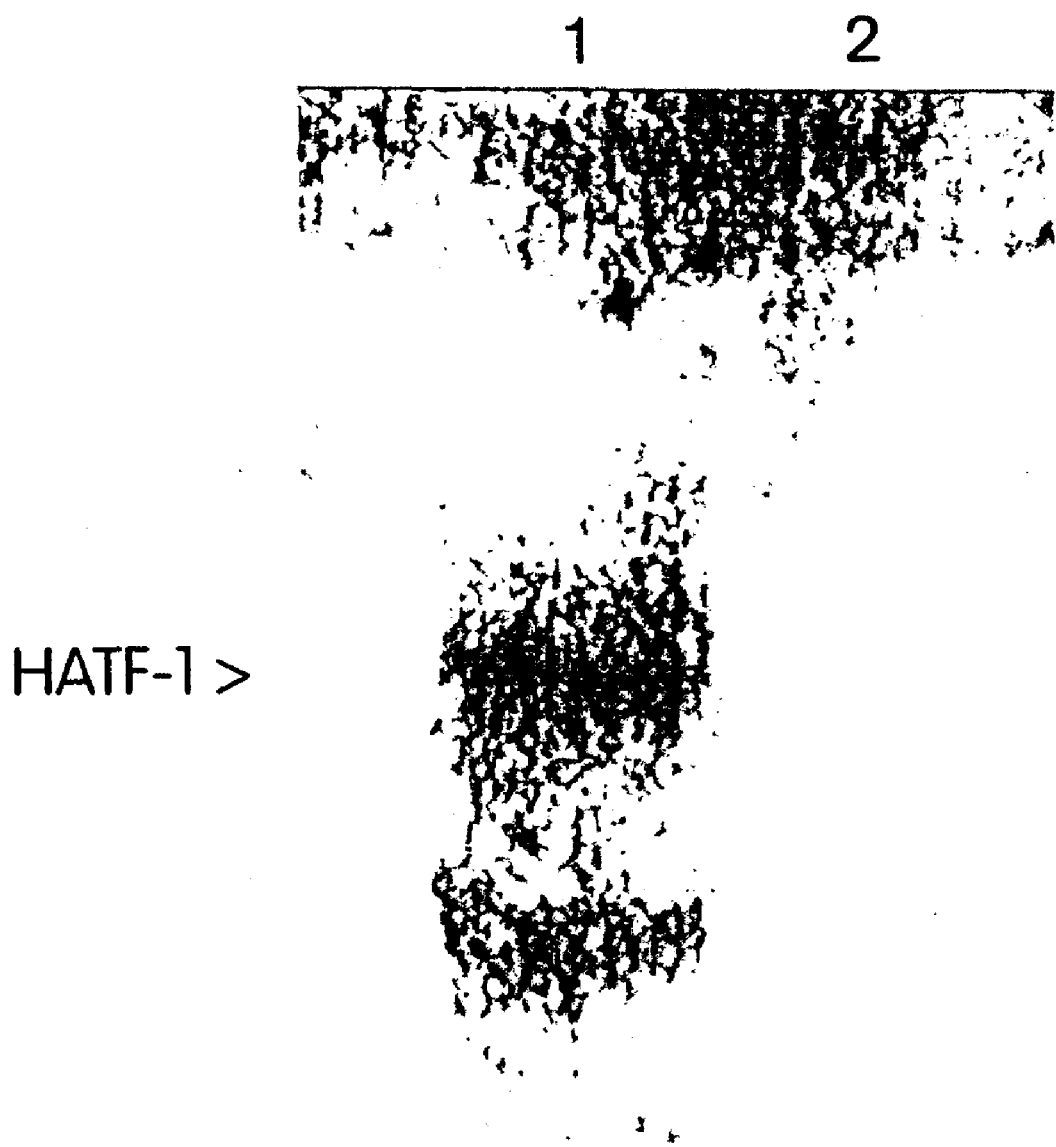

FIG. 6 is a gel depicting the differential expression of HATF-1 mRNA in cultured mesangial cells of hypertensive rats. HATF-1 mRNA levels are 4-fold higher in mesangial cells derived form the kidneys of SHR (lane 1) than WKY-derived mesangial cells (lane 2). Equivalent RNA loading was confirmed by visualization of ethidium bromide-stained 28 and 18S bands.

Figure 7A:
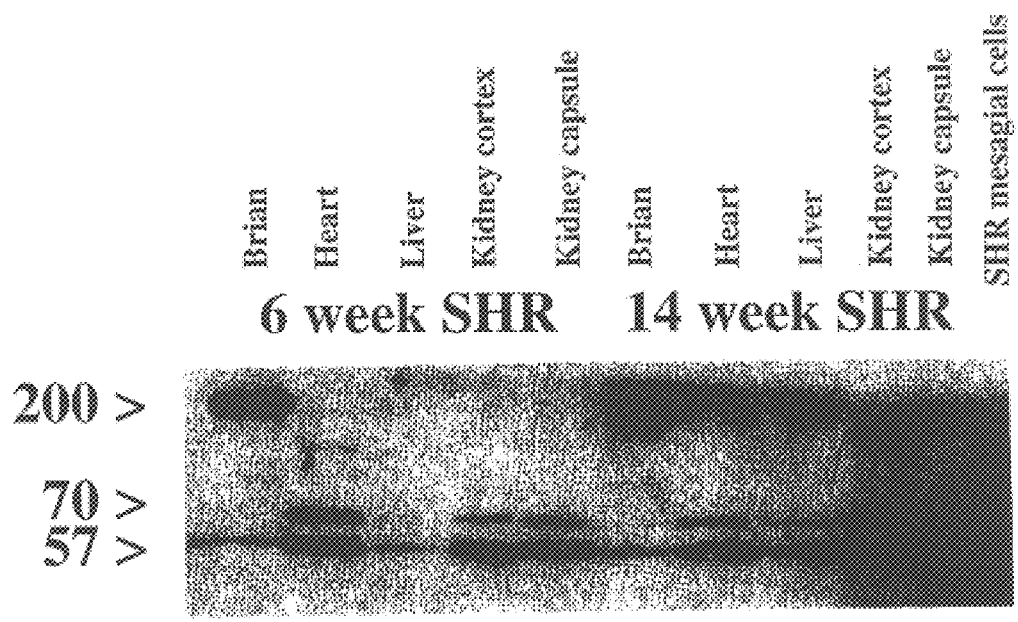
Figure 7B:
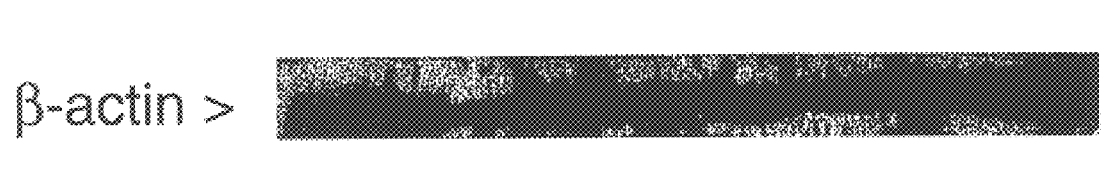

FIG. 7A is a gel depicting the tissue-specific distribution of multiple HATF-1 isoforms in hypertension-prone (6 week old) and adult hypertensive SHR. FIG. 7B is a gel depicting the β-actin control. Lanes 1–5, 6 week-old SHR, Lanes 6–10, 14 week-old SHR), lane 11, cultured SHR-derived mesangial cells.

Figures 8A, 8B:
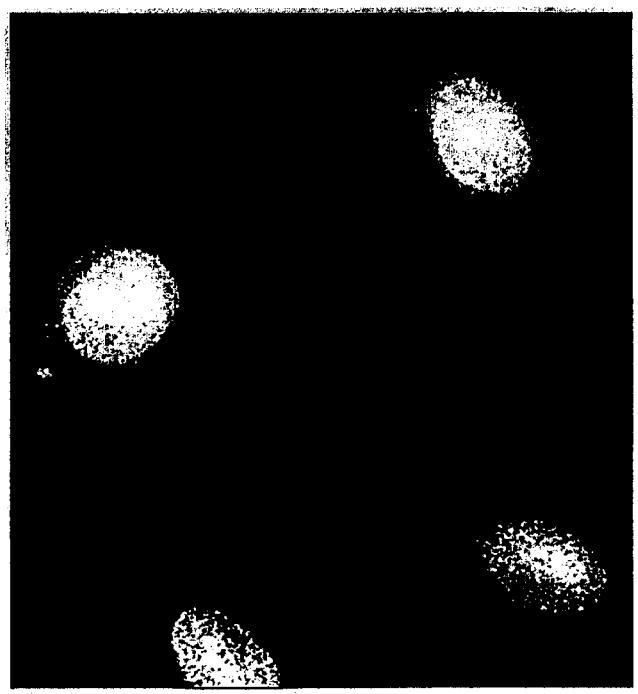

FIG. 8A depicts the results obtained from an immunofluorescence analysis indicating that HATF-1 protein is specifically localized in the nuclei of SHR-derived renal mesangial cells. FIG. 8B is a table indicating relative abundance of HATF-1 protein in the nuclei of SHR- and WKY-derived mesangial cells.

Figure 9A:
Figure 9B:
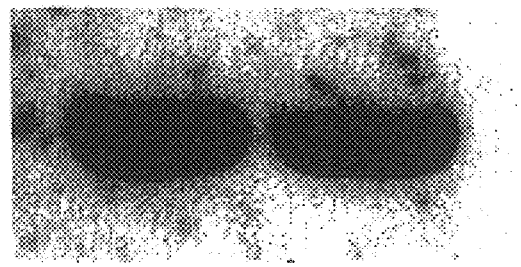

FIG. 9A is a gel indicating that HATF-1 protein levels are 2-fold higher in adult SHR-derived renal mesangial cells versus normotensive WKY. FIG. 9B is a gel indicating that the β-actin control levels are unchanged.

Figure 10A:
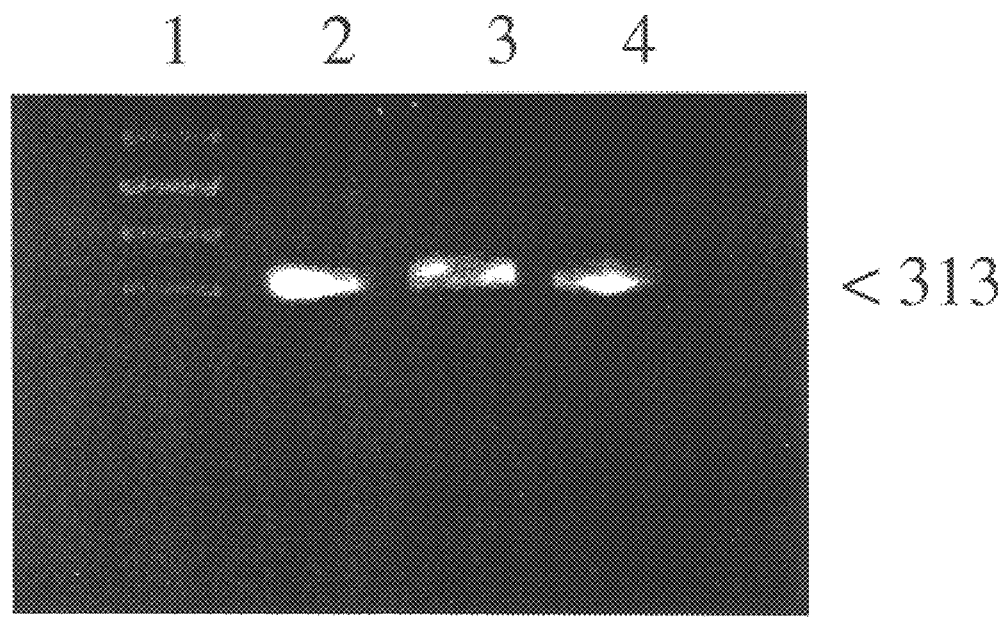
Figure 10B:
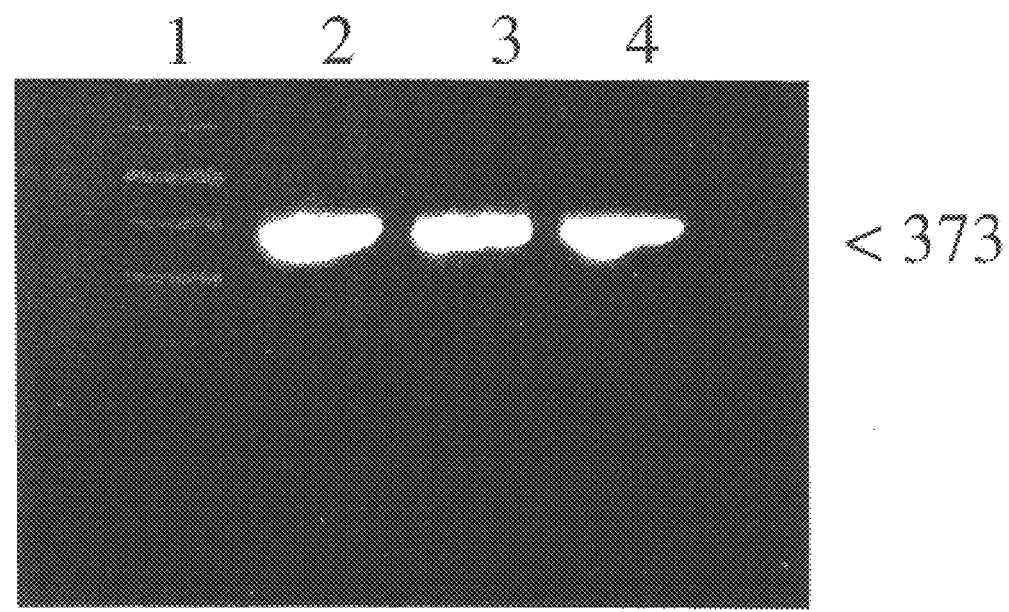

FIG. 10A is a gel depicting the identification of human and mouse HATF-1 orthologs. RT-PCR was performed using gene-specific primers for HATF-1. Lane 1. Marker; Lane 2. Rat; Lane 3. Human; Lane 4. Mouse. FIG. 10B is a gel depicting the β-actin control.

FIG. 11A depicts a sequence comparison of rat HATF-1 and human HATF-1 using the NBLAST program, a score of 100, and a wordlength of 12. Over 313 bp there is 100% identity. FIG. 11B depicts a sequence comparison of HATF-1 (upper strand, reverse complemented) and moused derived HRP-1 using the NBLAST program, a score of 100, and a wordlength of 12. Over 313 bp there is 87% identity.

FIG. 12 depicts the HATF-15' end amino acid (SEQ ID NO:2) and nucleotide sequence (SEQ ID NO:1).

FIG. 13 depicts the HATF-13' end amino acid (SEQ ID NO:4) and nucleotide sequence (SEQ ID NO:3).

FIG. 14 depicts the HRP-1 nucleotide sequence (SEQ ID NO:5).

DETAILED DESCRIPTION OF THE INVENTION

The present invention is based, at least in part, on the discovery of novel molecules, referred to herein as HATF-1 and HRP-1 nucleic acid and protein molecules which were identified and characterized using differential display RT-PCR and an animal model of hypertension. Expression of the HATF-1 mRNA precedes and is coincident with the onset of hypertension in the spontaneously hypertensive rat, a rodent model of essential hypertension.

Accordingly, the newly identified HATF-1 and HRP-1 nucleic acid and protein molecules can be used to identify cells exhibiting or predisposed to a cardiovascular disorder, e.g., hypertension, thereby diagnosing subjects having, or prone to developing such disorders. The HATF-1 and HRP-1 nucleic acid and protein molecules of the invention can further be used to treat subjects suffering from a cardiovascular disorder, e.g., hypertension.

As used herein, a "cardiovascular disorder" refers to a disorder, disease, or condition which affects the cardiovascular system, e.g., the heart, the blood vessels, or the blood. Cardiovascular disorders can be characterized by an inadequate supply of blood to an organ, e.g., the heart; the accumulation of fatty substances, e.g., cholesterol or triglycerides, in the walls of blood vessels; an irregularity in the heart rhythm; or a defective conduction of impulses from the atria to the ventricles of the heart. Examples of cardiovascular disorders include heart failure, hypertension, atherosclerosis, coronary artery disease, coronary artery spasm, arrythmias, atrial fibrillation, dilated cardiomyopathy, idiopathic cardiomyopathy, or angina.

The newly identified HATF-1 and HRP-1 nucleic acid and protein molecules can further be used to identify cells exhibiting or predisposed to a renal disorder, e.g., glumerulonephritis, thereby diagnosing subjects having, or prone to developing such disorders. The HATF-1 and HRP-1 nucleic acid and protein molecules of the invention can further be used to treat subjects suffering from a renal disorder, e.g., glumerulonephritis.

As used herein, a "renal disorder" refers to a disorder, disease, or condition which affects the kidney. Examples of such disorders include glumerulonephritis (Bright's disease), nephritis, pyelitis, pyelonephritis, and renal calculi.

As used herein, "differential expression" or "differentially expressed" includes both quantitative as well as qualitative differences in the temporal and/or cellular expression pattern of a gene, e.g., the HATF-1 and HRP-1 gene, among, for example, normotensive and hypertensive cells. Genes which are differentially expressed can be used as part of a prognostic or diagnostic marker for the evaluation of subjects at risk for developing a cardiovascular disorder, e.g., hypertension. Depending on the expression level of the gene, the progression state of the disorder can also be evaluated.

One embodiment of the invention features HATF-1 and HRP-1 nucleic acid molecules, e.g., human, rat, and mouse HATF-1 and HRP-1, which were identified using differential mRNA expression analysis.

The HATF-1 and HRP-1 Nucleic Acid and Protein Molecules

The present invention is based, at least in part, on the discovery of novel molecules, referred to herein as HATF-1 and HRP-1 protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

In one embodiment, the isolated HATF-1 and HRP-1 proteins of the present invention are identified based on the presence of at least one or more of a "zinc finger." As used herein, the term "zinc finger" includes an amino acid sequence of about 15–25 amino acid residues in length, preferably about 18–22 amino acid residues in length, and most preferably about 20–22 amino acid residues in length, which selectively binds a zinc ion. Zinc fingers are usually found in DNA-binding proteins, e.g., transcription factors. In a preferred embodiment, a zinc finger can have the following consensus sequence:Cys-$X_{2-4}$-Cys-$X_{1-3}$-Phe-$X_5$-Leu-$X_2$-His-$X_3$-His (SEQ ID NO:19). Amino acid residues 5–27, 61–81, 89–109, 139–159, 167–187, 272–292, and 363–383 of the HATF-1 and HRP-1 proteins comprise zinc fingers.

Isolated proteins of the present invention, preferably HATF-1 and HRP-1 proteins, have an amino acid sequence sufficiently homologous to the amino acid sequence of SEQ ID NO:2 or 4, or are encoded by a nucleotide sequence sufficiently homologous to SEQ ID NO:1, 3, and/or 5. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%, 80%, and even more preferably 90%, 95%, or 98% homology across the amino acid sequences of the domains and contain at least one and preferably two structural domains or motifs, are defined herein as sufficiently homologous. Furthermore, amino acid or nucleotide sequences which share at least 30%, 40%, or 50%, preferably 60%, more preferably 70–80%, or 90–95% homology and share a common functional activity are defined herein as sufficiently homologous.

As used interchangeably herein an "HATF-1 activity" or "HRP-1 activity"; "biological activity of HATF-1" or "biological activity of HRP-1"; or "functional activity of HATF-1" or "functional activity of HRP-1", refers to an activity exerted by an HATF-1 and/or HRP-1 protein, polypeptide or nucleic acid molecule on an HATF-1 and/or HRP-1 responsive cell as determined in vivo, or in vitro, according to standard techniques. The biological activities of HATF-1 and HRP-1 are described herein. Preferably, an HATF-1 and HRP-1 polypeptide of the present invention can have one or more of the following activities: (a) it can act as a transcriptional regulator; (b) it can modulate the onset as well as the progression of hypertension, e.g., cerebral or renal hypertension, by, for example, having an effect on the physiology or function of endothelial or mesangial cells; (c) it can modulate the expression of vasoconstrictive substances, e.g., endothelium-derived relaxing factor (EDRF), endothelium-derived constricting factor (EDCF), endothelin-1, the catecholamines, the endothelins, or the renin-angiogenic system; (d) it can modulate nitric oxide (NO) receptor levels, e.g., NO receptor levels on endothelial cells; (e) it can modulate mesangial cell proliferation or function; and (f) it can modulate smooth muscle cell proliferation, reactivity, contractility, and/or function.

Accordingly, another embodiment of the invention features isolated HATF-1 and HRP-1 proteins and polypeptides having an HATF-1 or an HRP-1 activity. Preferred proteins are HATF-1 and HRP-1 proteins having at least one, two, three, four, five, six, or seven zinc fingers and, preferably, an HATF-1 or an HRP-1 activity. Additional preferred proteins have at least one, two, three, four, five, six, or seven zinc fingers and are, preferably, encoded by a nucleic acid molecule having a nucleotide sequence which hybridizes under stringent hybridization conditions to a nucleic acid molecule comprising the nucleotide sequence of SEQ ID NO:1, 3, and/or 5.

The 5' end nucleotide and amino acid sequence of the isolated human, rat, and mouse HATF-1 is shown in FIG. 12 and in SEQ ID NO:1 and SEQ ID NO:2, respectively.

The 3' end nucleotide and amino acid sequence of the isolated human, rat, and mouse HATF-1 is shown in FIG. 13 and in SEQ ID NO:3 and SEQ ID NO:4, respectively.

The nucleotide sequence of the isolated mouse HRP-1 is shown in FIG. 14 and in SEQ ID NO:5.

Various aspects of the invention are described in further detail in the following subsections:

1. Differentially Expressed Nucleic Acid Molecules

One aspect of the invention pertains to isolated HATF-1 and HRP-1 nucleic acid molecules or biologically active portions thereof, which are differentially expressed in cells, e.g., cerebrovascular endothelial cells, of hypertensive subjects, e.g., humans or rats. The invention further pertains to HATF-1 and HRP-1 nucleic acid fragments sufficient for use as hybridization probes to identify HATF-1 and HRP-1-encoding nucleic acid molecules (e.g., HATF-1 and HRP-1 mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated HATF-1 and HRP-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a brain cell or other cell that expresses HATF-1 or HRP-1). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO:1, 3, and/or 5, or a portion thereof, can be isolated using standard molecular biology techniques and the sequence information provided herein. For example, a human HATF-1 and HRP-1 cDNA can be isolated from a human brain library, using all or portion of SEQ ID NO:1, 3, and/or 5 as a hybridization probe and standard hybridization techniques (e.g., as described in Sambrook, J., Fritsh, E. F., and Maniatis, T. *Molecular Cloning: A Laboratory Manual*. 2nd, ed, Cold Spring Harbor Laboratory, Cold Spring Harbor Laboratory Press, Cold Spring Harbor, N.Y., 1989). Moreover, a nucleic acid molecule encompassing all or a portion of SEQ ID NO:1, 3, and/or 5 can be isolated by the polymerase chain reaction using oligonucleotide primers designed based upon the sequence of SEQ ID NO:1, 3, and/or 5. For example, mRNA can be isolated from cerebrovascular endothelial cells of hypertensive subjects (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/ BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1, 3, and/or 5. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an HATF-1 and HRP-1 nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1, 3, and/or 5. The sequence of SEQ ID NO:1 and 3 corresponds to the human, rat, and mouse HATF-1 cDNA. The sequence of SEQ ID NO:5 corresponds to the mouse HRP-1 cDNA. The HATF-1 and HRP-1 cDNAs comprise sequences encoding the human, rat, and mouse HATF-1 and the mouse HRP-1 protein (i.e., "the coding region"), as well as 5' untranslated sequences and 3' untranslated sequences. Alternatively, the nucleic acid molecule can comprise only the coding region of SEQ ID NOs:1, 3, and/or 5.

In another preferred embodiment, an isolated nucleic acid molecule of the invention comprises a nucleic acid molecule which is a complement of the nucleotide sequence shown in SEQ ID NO:1, 3, and/or 5, or a portion of any of these nucleotide sequences. A nucleic acid molecule which is complementary to the nucleotide sequence shown in SEQ ID NO:1, 3, and/or 5, is one which is sufficiently complementary to the nucleotide sequence shown in SEQ ID NO:1, 3, and/or 5, such that it can hybridize to the nucleotide sequence shown in SEQ ID NO:1, 3, and/or 5, thereby forming a stable duplex.

In still another preferred embodiment, an isolated nucleic acid molecule of the present invention comprises a nucleotide sequence which is at least about 50%, 55%, 60%, 65%, 70%, 73%, 75%, 80%, 85%, 86%, 87%, 89%, 90%, 95%, 98% or more homologous to the entire length of the nucleotide sequence shown in SEQ ID NO:1, 3, or 5 or a portion thereof.

Moreover, the nucleic acid molecule of the invention can comprise only a portion of the nucleic acid sequence of SEQ ID NO:1, 3, or 5, for example a fragment which can be used as a probe or primer. The nucleotide sequence determined from the cloning of the HATF-1 and HRP-1 gene allows for the generation of probes and primers designed for use in identifying and/or cloning other HATF-1 and HRP-1 family members, as well as HATF-1 and HRP-1 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, 75, 80, 85, 90, 95, 100, or more consecutive nucleotides of a sense sequence of SEQ ID NO:1, 3, and/or 5, of an anti-sense sequence of SEQ ID NO:1, 3, and/or 5, or of a naturally occurring allelic variant or mutant of SEQ ID NO:1, 3, and/or 5. In an exemplary embodiment, a nucleic acid molecule of the present invention comprises a nucleotide sequence which is greater than 100, 150, 200, 200–250, 250–300, 300–350, 350–400, 450–500, 500–550, 550–600, 600–650, 650–700, 700–750, 750–800, 800–850, 850–900, 950–1000, or more nucleotides in length and hybridizes under stringent hybridization conditions to a nucleic acid molecule of SEQ ID NO:1, 3, and/or 5.

Probes based on the HATF-1 and HRP-1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic or prognostic test kit for identifying cells or tissues which misexpress or differentially express an HATF-1 and HRP-1 protein, such as by measuring a level of an HATF-1 or HRP-1-encoding nucleic acid in a sample of cells from a subject e.g., detecting HATF-1 and HRP-1 mRNA levels or determining whether a genomic HATF-1 and HRP-1 gene has been mutated or deleted.

The invention further encompasses nucleic acid molecules that differ from the nucleotide sequence shown in SEQ ID NO:1, 3, or 5, due to degeneracy of the genetic code and thus encode the same HATF-1 and HRP-1 proteins as those encoded by the nucleotide sequence shown in SEQ ID NO:1, 3, and/or 5. In another embodiment, an isolated nucleic acid molecule of the invention has a nucleotide sequence encoding a protein having an amino acid sequence shown in SEQ ID NO:2 or 4.

In addition to the HATF-1 and HRP-1 nucleotide sequences shown in SEQ ID NO:1, 3, or 5, it will be appreciated by those skilled in the art that DNA sequence polymorphisms that lead to changes in the amino acid sequences of the HATF-1 and HRP-1 proteins may exist within a population (e.g., the human population). Such genetic polymorphism in the HATF-1 and HRP-1 genes may exist among individuals within a population due to natural allelic variation. Such natural allelic variations can typically result in 1–5% variance in the nucleotide sequence of an HATF-1 and HRP-1 gene. Any and all such nucleotide variations and resulting amino acid polymorphisms in HATF-1 and HRP-1 genes that are the result of natural allelic variation and that do not alter the functional activity of an HATF-1 and HRP-1 protein are intended to be within the scope of the invention.

Moreover, nucleic acid molecules encoding other HATF-1 and HRP-1 family members and, thus, which have a nucleotide sequence which differs from the HATF-1 and HRP-1 sequences of SEQ ID NO:1, 3, and/or 5 are intended to be within the scope of the invention. For example, another HATF-1 and HRP-1 cDNA can be identified based on the nucleotide sequence of rat HATF-1 or HRP-1. Moreover, nucleic acid molecules encoding HATF-1 and HRP-1 proteins from different species, and thus which have a nucleotide sequence which differs from the HATF-1 and HRP-1 sequences of SEQ ID NO:1, 3, and/or 5 are intended to be within the scope of the invention. For example, a human HRP-1 cDNA can be identified based on the nucleotide sequence of a mouse HRP-1.

Nucleic acid molecules corresponding to natural allelic variants and homologues of the HATF-1 and HRP-1 cDNAs of the invention can be isolated based on their homology to the HATF-1 and HRP-1 nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 3, and/or 5. In other embodiments, the nucleic acid is at least 30, 50, 100, 150, 200, 250, 300, 350, 400, 450, 500, 550, 600, 650, 700, 750, 800, 850, 900, or 950 nucleotides in length. As used herein, the term "hybridizes under stringent conditions" is intended to describe conditions for hybridization and washing under which nucleotide sequences of a particular length and nucleic acid content will remain hybridized to each other. Homologous or related nucleic acid sequences will remain hybridized under stringent conditions. For example, stringent hybridization conditions are such that sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50° C., 55° C., 60° C., or 65° C. Preferably, an isolated nucleic acid molecule of the invention that hybridizes under stringent conditions to the sequence of SEQ ID NO:1, 3, or 5 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to the nucleic acid molecules encoding HATF-1 and HRP-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire HATF-1 and HRP-1 coding strand, or to only a portion thereof. In one embodiment, an antisense nucleic acid molecule is antisense to a "coding region" of the coding strand of a nucleotide sequence encoding HATF-1 or HRP-1. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding HATF-1 or HRP-1. The term "noncoding region" refers to 5' and 3' sequences which flank the coding region that are not translated into amino acids (i.e., also referred to as 5' and 3' untranslated regions).

Given the HATF-1 and HRP-1 nucleic acid molecules disclosed herein (e.g., SEQ ID NO:1, 3, and 5), antisense nucleic acids of the invention can be designed according to the rules of Watson and Crick base pairing. The antisense nucleic acid molecule can be complementary to the entire HATF-1 or HRP-1 nucleic acid molecule, but more preferably is an oligonucleotide which is antisense to only a portion of the HATF-1 or HRP-1 nucleic acid molecule. For example, the antisense oligonucleotide can be complementary to the region surrounding the translation start site of HATF-1 or HRP-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an HATF-1 and HRP-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave HATF-1 or HRP-1 mRNA transcripts to thereby inhibit translation of HATF-1 or HRP-1 mRNA. A ribozyme having specificity for an HATF-1 or HRP-1-encoding nucleic acid can be designed based upon the nucleotide sequence of an HATF-1 or HRP-1 cDNA disclosed herein (i.e., SEQ ID NO:1, 3, and/or 5). For example, a derivative of a *Tetrahymena L-19 IVS RNA* can be constructed in which the nucleotide sequence of the active site is complementary to the nucleotide sequence to be cleaved in an HATF-1 or HRP-1-encoding mRNA. See, e.g., Cech et al. U.S. Pat. No. 4,987,071; and Cech et al. U.S. Pat. No. 5,116,742. Alternatively, HATF-1 and HRP-1 mRNA can be used to select a catalytic RNA having a specific ribonuclease activity from a pool of RNA molecules. See, e.g., Bartel, D. and Szostak, J. W. (1993) *Science* 261:1411–1418.

Alternatively, HATF-1 or HRP-1 gene expression can be inhibited by targeting nucleotide sequences complementary to the regulatory region of the HATF-1 or HRP-1 (e.g., the HATF-1 or HRP-1 promoter and/or enhancers) to form triple helical structures that prevent transcription of the HATF-1 or HRP-1 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the HATF-1 and HRP-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of HATF-1 and HRP-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of HATF-1 and HRP-1 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of HATF-1 and HRP-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of HATF-1 and HRP-1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

In addition to naturally-occurring allelic variants of the HATF-1 and HRP-1 sequences that may exist in the population, the skilled artisan will further appreciate that changes can be introduced by mutation into the nucleotide sequences of SEQ ID NO:1, 3, and/or 5, thereby leading to changes in the amino acid sequence of the encoded HATF-1 and HRP-1 proteins, without altering the functional ability of the HATF-1 and HRP-1 proteins. For example, nucleotide substitutions leading to amino acid substitutions at "non-essential" amino acid residues can be made in the sequence of SEQ ID NO:1, 3, and/or 5. A "non-essential" amino acid residue is a residue that can be altered from the wild-type sequence of HATF-1 and HRP-1 (e.g., the sequence of SEQ ID NO:2 or 4) without altering the biological activity, whereas an "essential" amino acid residue is required for biological activity. For example, amino acid residues that are conserved among the HATF-1 and HRP-1 proteins of the present invention, are predicted to be particularly unamenable to alteration, e.g., the cysteine residues in the zinc finger motifs.

Accordingly, another aspect of the invention pertains to nucleic acid molecules encoding HATF-1 and HRP-1 proteins that contain changes in amino acid residues that are not essential for activity. Such HATF-1 and HRP-1 proteins differ in amino acid sequence from SEQ ID NO:2 or 4, yet retain biological activity. In one embodiment, the isolated nucleic acid molecule comprises a nucleotide sequence encoding a protein, wherein the protein comprises an amino acid sequence at least about 40%, 45%, 50%, 55%, 60%, 65%, 70%, 75%, 80%, 85%, 90%, 95% 98% or more homologous to SEQ ID NO:2 or 4.

An isolated nucleic acid molecule encoding an HATF-1 or HRP-1 protein homologous to the protein of SEQ ID NO:2 or 4 can be created by introducing one or more nucleotide substitutions, additions or deletions into the nucleotide sequence of SEQ ID NO:1, 3, and/or 5, such that one or more amino acid substitutions, additions or deletions are introduced into the encoded protein. Mutations can be introduced into SEQ ID NO:1, 3, and/or 5 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an HATF-1 and HRP-1 protein is preferably replaced with another amino acid residue from the same side chain family. Alternatively, in another embodiment, mutations can be introduced randomly along all or part of an HATF-1 and HRP-1 coding sequence, such as by saturation mutagenesis, and the resultant mutants can be screened for HATF-1 and HRP-1 biological activity to identify mutants that retain activity. Following mutagenesis of SEQ ID NO:1, 3, and/or 5, the encoded protein can be expressed recombinantly and the activity of the protein can be determined.

In a preferred embodiment, a mutant HATF-1 and HRP-1 protein can be assayed for the ability to (a) act as a transcriptional regulator; (b) modulate the onset as well as the progression of hypertension, e.g., cerebral or renal hypertension, by, for example, having an effect on the physiology or function of endothelial or mesangial cells; (c) modulate the expression of vasoconstrictive substances, e.g., endothelium-derived relaxing factor (EDRF), endothelium-derived constricting factor (EDCF), endothelin-1, the catecholamines, the endothelins, or the renin-angiogenic system; (d) modulate nitric oxide (NO) receptor levels, e.g., NO receptor levels on endothelial cells; (e) modulate mesangial cell proliferation or function; and (f) modulate smooth muscle cell proliferation, reactivity, contractility, and/or function.

II. Uses and Methods of the Invention

The compositions described herein, particularly the differentially expressed HATF-1 and HRP-1 nucleic acid molecules, as well as the proteins, protein homologues, and antibodies described herein can be used in one or more of the following methods: a) predictive medicine (e.g., diagnostic assays, prognostic assays, monitoring clinical trials, and pharmacogenetics); b) methods of treatment (e.g., therapeutic and prophylactic); c) detection assays; and d) screening assays. As described herein, HATF-1 and HRP-1 nucleic acid molecules are differentially expressed in hypertensive rats. Accordingly, the isolated nucleic acid molecules of the invention can be used to, for example, detect HATF-1 or HRP-1 mRNA (e.g., in a biological sample) or a genetic alteration in an HATF-1 or an HRP-1 gene, to thereby diagnose subjects having, or prone to developing a cardiovascular disorder, e.g., heart failure, hypertension, atherosclerosis, coronary artery disease, coronary artery spasm, arrythmias, atrial fibrillation, dilated cardiomyopathy, idiopathic cardiomyopathy, or angina. The isolated nucleic acid molecules of the invention can further be used to modulate HATF-1 or HRP-1 activity, or express an HATF-1 or HRP-1 protein (e.g., via a recombinant expression vector in a host cell in gene therapy applications), as described further below.

A. Predictive Medicine:

The present invention pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining HATF-1 or HRP-1 nucleic acid and/or protein expression as well as HATF-1 or HRP-1 activity, in the context of a biological sample (e.g., blood, serum, cells, or tissue) to thereby determine whether a subject is afflicted with a disease or disorder, or is at risk of developing a disorder, associated with aberrant HATF-1 or HRP-1 expression or activity. The invention also provides for prognostic (or predictive) assays for determining whether an individual is at risk of developing a disorder associated with HATF-1 or HRP-1 protein, nucleic acid expression or activity. For example, mutations in an HATF-1 or an HRP-1 gene can be assayed in a biological sample. Such assays can be used for prognostic or predictive purposes to, thereby, phophylactically treat a subject prior to the onset of a disorder characterized by or associated with an HATF-1 or an HRP-1 protein, nucleic acid expression or activity.

Another aspect of the invention pertains to monitoring the influence of agents (e.g., drugs, compounds) on the expression or activity of HATF-1 or HRP-1 in clinical trials.

These and other agents are described in further detail in the following sections.

1. Diagnostic Assays

An exemplary method for detecting the presence or absence of HATF-1 or HRP-1 nucleic acid or protein in a biological sample involves obtaining a biological sample from a test subject and contacting the biological sample with a compound or an agent capable of detecting HATF-1 or HRP-1 nucleic acid or protein (e.g., mRNA, genomic DNA, or antibody) such that the presence of HATF-1 or HRP-1 nucleic acid or protein is detected in the biological sample. A preferred agent for detecting HATF-1 or HRP-1 mRNA or genomic DNA is a labeled nucleic acid probe capable of hybridizing to HATF-1 or HRP-1 mRNA or genomic DNA.

The nucleic acid probe can be, for example, a full-length HATF-1 or HRP-1 nucleic acid, or a portion thereof such as the nucleic acid of SEQ ID NO:1, 3, and/or 5, or an oligonucleotide of at least 15, 20, 25, 30, 35, 40, 45, 50, 100, 250 or 500 nucleotides in length and sufficient to specifically hybridize under stringent conditions to HATF-1 or HRP-1 mRNA or genomic DNA. Other suitable probes for use in the diagnostic assays of the invention are described herein.

A preferred agent for detecting HATF-1 or HRP-1 protein is an antibody capable of binding to HATF-1 or HRP-1 protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect HATF-1 or HRP-1 mRNA, genomic DNA, or protein in a biological sample in vitro as well as in vivo. For example, in vitro techniques for detection of HATF-1 or HRP-1 mRNA include Northern hybridizations and in situ hybridizations. In vitro techniques for detection of HATF-1 or HRP-1 protein include enzyme linked immunosorbent assays (ELISAs), Western blots, immunoprecipitations and immunofluorescence. In vitro techniques for detection of HATF-1 or HRP-1 genomic DNA include Southern hybridizations. Furthermore, in vivo techniques for detection of HATF-1 or HRP-1 protein include introducing into a subject a labeled anti-HATF-1 or HRP-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting HATF-1 or HRP-1 mRNA, genomic DNA, or protein, such that the presence of HATF-1 or HRP-1 mRNA genomic DNA or protein is detected in the biological sample, and comparing the presence of HATF-1 or HRP-1 mRNA, genomic DNA, or protein in the control sample with the presence of HATF-1 or HRP-1 mRNA, genomic DNA, or protein in the test sample.

The invention also encompasses kits for detecting the presence of HATF-1 or HRP-1 in a biological sample. For example, the kit can comprise a labeled compound or agent capable of detecting HATF-1 or HRP-1 DNA, mRNA, or protein in a biological sample; means for determining the amount of HATF-1 or HRP-1 in the sample; and means for comparing the amount of HATF-1 or HRP-1 in the sample with a standard. The compound or agent can be packaged in a suitable container. The kit can further comprise instructions for using the kit to detect HATF-1 or HRP-1 nucleic acid or protein.

2. Prognostic Assays

The diagnostic methods described herein can furthermore be utilized to identify subjects having or at risk of developing a disease or disorder associated with aberrant HATF-1 or HRP-1 expression or activity. For example, the assays described herein, such as the preceding diagnostic assays or the following assays, can be utilized to identify a subject having or at risk of developing a disorder associated with a misregulation in HATF-1 or HRP-1 protein activity or nucleic acid expression, such as a cardiovascular disorder. Thus, the present invention provides a method for identifying a disease or disorder associated with aberrant HATF-1 or HRP-1 expression or activity, in which a test sample is obtained from a subject and HATF-1 or HRP-1 nucleic acid (e.g., mRNA or genomic DNA) or protein is detected, wherein the presence of HATF-1 or HRP-1 protein or nucleic acid is diagnostic for a subject having or at risk of developing a disease or disorder associated with aberrant HATF-1 or HRP-1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant HATF-1 or HRP-1 expression or activity. For example, such methods can be used to determine whether a subject can be effectively treated with an agent for a cardiovascular disorder, e.g., hypertension. Thus, the present invention provides methods for determining whether a subject can be effectively treated with an agent for a disorder associated with aberrant HATF-1 or HRP-1 expression or activity in which a test sample is obtained and HATF-1 or HRP-1 protein or nucleic acid expression or activity is detected (e.g., wherein the abundance of HATF-1 or HRP-1 nucleic acid or protein expression or activity is diagnostic for a subject that can be administered the agent to treat a disorder associated with aberrant HATF-1 or HRP-1 expression or activity).

The methods of the invention can also be used to detect genetic alterations in an HATF-1 or HRP-1 gene, thereby determining if a subject with the altered gene is at risk for a disorder characterized by misregulation in HATF-1 or HRP-1 protein activity or nucleic acid expression, such as a cardiovascular disorder. In preferred embodiments, the methods include detecting, in a sample of cells from the subject, the presence or absence of a genetic alteration characterized by at least one of an alteration affecting the integrity of a gene encoding an HATF-1 or HRP-1-protein, or the mis-expression of the HATF-1 or HRP-1 gene. For example, such genetic alterations can be detected by ascertaining the existence of at least one of 1) a deletion of one or more nucleotides from an HATF-1 or HRP-1 gene; 2) an addition of one or more nucleotides to an HATF-1 or HRP-1 gene; 3) a substitution of one or more nucleotides of an HATF-1 or HRP-1 gene, 4) a chromosomal rearrangement of an HATF-1 or HRP-1 gene; 5) an alteration in the level of a messenger RNA transcript of an HATF-1 or HRP-1 gene, 6) aberrant modification of an HATF-1 or HRP-1 gene, such as of the methylation pattern of the genomic DNA, 7) the presence of a non-wild type splicing pattern of a messenger RNA transcript of an HATF-1 or HRP-1 gene, 8) a non-wild type level of an HATF-1 or HRP-1-protein, 9) allelic loss of an HATF-1 or HRP-1 gene, and 10) inappropriate post-translational modification of an HATF-1 or HRP-1-protein. As described herein, there are a large number of assays known in the art which can be used for detecting alterations in an HATF-1 or HRP-1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the HATF-1 or HRP-1-gene (see Abravaya et al. (1995) Nucleic Acids Res. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an HATF-1 or HRP-1 gene under conditions such that hybridization and amplification of the HATF-1 or HRP-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874–1878), transcriptional amplification system (Kwoh, D. Y. et al., (1989) Proc. Natl. Acad. Sci. USA 86:1173–1177), Q-Beta Replicase (Lizardi, P. M. et al. (1 988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an HATF-1 or HRP-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in HATF-1 or HRP-1 can be identified by hybridizing a sample and control nucleic acids, e.g., DNA or RNA, to high density arrays containing hundreds or thousands of oligonucleotides probes (Cronin, M. T. et al. (1996) Human Mutation 7: 244–255; Kozal, M. J. et al. (1996) Nature Medicine 2: 753–759). For example, genetic mutations in HATF-1 or HRP-1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the HATF-1 or HRP-1 gene and detect mutations by comparing the sequence of the sample HATF-1 or HRP-1 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO94/16101; Cohen et al. (1996) Adv. Chromatogr. 36:127–162; and Griffin et al. (1993) Appl. Biochem. Biotechnol. 38:147–159).

Other methods for detecting mutations in the HATF-1 or HRP-1 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type HATF-1 or HRP-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl Acad Sci USA 85:4397; Saleeba et al. (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in HATF-1 or HRP-1 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on an HATF-1 or HRP-1 sequence, e.g., a wild-type HATF-1 or HRP-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in HATF-1 or HRP-1 genes. For example, single strand conformation polymorphism (SSCP) may be used to detect differences in electrophoretic mobility between mutant and wild type nucleic acids (orita et al. (1989) *Proc Natl. Acad Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control HATF-1 or HRP-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an HATF-1 or HRP-1 gene.

Furthermore, any cell type or tissue in which HATF-1 or HRP-1 is expressed may be utilized in the prognostic assays described herein.

3. Monitoring of Effects During Clinical Trials

Monitoring the influence of agents (e.g., drugs) on the expression or activity of an HATF-1 or HRP-1 protein can be applied not only in basic drug screening, but also in clinical trials. For example, the effectiveness of an agent determined by a screening assay as described herein to decrease HATF-1 or HRP-1 gene expression, protein levels, or downregulate HATF-1 or HRP-1 activity, can be monitored in clinical trials of subjects exhibiting increased HATF-1 or HRP-1 gene expression, protein levels, or upregulated HATF-1 or HRP-1 activity. Alternatively, the effectiveness of an agent determined by a screening assay to increase HATF-1 or HRP-1 gene expression, protein levels, or upregulate HATF-1 or HRP-1 activity, can be monitored in clinical trials of subjects exhibiting decreased HATF-1 or HRP-1 gene expression, protein levels, or downregulated HATF-1 or HRP-1 activity. In such clinical trials, the expression or activity of an HATF-1 or HRP-1 gene, and preferably, other genes that have been implicated in, for example, an HATF-1 or HRP-1-associated disorder can be used as a "read out" or markers of the phenotype of a particular cell.

For example, and not by way of limitation, genes, including HATF-1 or HRP-1, that are modulated in cells by treatment with an agent (e.g., compound, drug or small molecule) which modulates HATF-1 or HRP-1 activity (e.g., identified in a screening assay as described herein) can be identified. Thus, to study the effect of agents on HATF-1 or HRP-1-associated disorders (e.g., cardiovascular disorders), for example, in a clinical trial, cells can be isolated and RNA prepared and analyzed for the levels of expression of HATF-1 or HRP-1 and other genes implicated in the HATF-1 or HRP-1-associated disorder, respectively. The levels of gene expression (e.g., a gene expression pattern) can be quantified by northern blot analysis or RT-PCR, as described herein, or alternatively by measuring the amount of protein produced, by one of the methods described herein, or by measuring the levels of activity of HATF-1 or HRP-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an HATF-1 or HRP-1 mRNA, genomic DNA, or protein in the pre-administration sample; (iii) obtaining one or more post-administration samples from the subject; (iv) detecting the level of expression or activity of the HATF-1 or HRP-1 mRNA, genomic DNA, or protein in the post-administration samples; (v) comparing the level of expression or activity of the HATF-1 or HRP-1 mRNA, genomic DNA, or protein in the pre-administration sample with the HATF-1 or HRP-1 mRNA, genomic DNA, or protein in the post administration sample or samples; and (vi) altering the administration of the agent to the subject accordingly. For example, increased administration of the agent may be desirable to decrease the expression or activity of HATF-1 or HRP-1 to lower levels than detected, i.e., to increase the effectiveness of the agent. Alternatively, decreased administration of the agent may be desirable to increase expression or activity of HATF-1 or HRP-1 to higher levels than detected, i.e. to decrease the effectiveness of the agent. According to such an embodiment, HATF-1 or HRP-1 expression or activity may be used as an indicator of the effectiveness of an agent, even in the absence of an observable phenotypic response.

B. Methods of Treatment:

The present invention provides for both prophylactic and therapeutic methods of treating a subject at risk of (or susceptible to) or having a disorder associated with aberrant HATF-1 or HRP-1 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the HATF-1 or HRP-1 molecules of the present invention or HATF-1 or HRP-1 modulators according to that individual's drug response genotype. Pharmacogenomics allow a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant HATF-1 or HRP-1 expression or activity, by administering to the subject an HATF-1 or HRP-1 or an agent which modulates HATF-1 or HRP-1 expression or at least one HATF-1 or HRP-1 activity. Subjects at risk for a disease which is caused or contributed to by aberrant HATF-1 or HRP-1 expression or activity can be identified by, for example, any or a combination of diagnostic or prognostic assays as described herein. Administration of a prophylactic agent can occur prior to the manifestation of symptoms characteristic of the HATF-1 or HRP-1 aberrancy, such that a disease or disorder is prevented or, alternatively, delayed in its progression. Depending on the type of HATF-1 or HRP-1 aberrancy, for example, an HATF-1 or HRP-1 molecule, HATF-1 or HRP-1 agonist or HATF-1 or HRP-1 antagonist can be used for treating the subject. The appropriate agent can be determined based on screening assays described herein.

2. Therapeutic Methods

Another aspect of the invention pertains to methods of modulating HATF-1 or HRP-1 expression or activity for therapeutic purposes. Accordingly, in an exemplary embodiment, the modulatory method of the invention involves contacting a cell with an HATF-1 or HRP-1 molecule or an agent which modulates (e.g., upregulates or downregulates) HATF-1 or HRP-1 expression or activity. In another embodiment, the method involves administering an HATF-1 or HRP-1 protein or nucleic acid molecule as therapy to compensate for reduced or aberrant HATF-1 or HRP-1 expression or activity.

In another embodiment, the agent inhibits one or more HATF-1 or HRP-1 activities. Examples of such inhibitory agents include antisense HATF-1 or HRP-1 nucleic acid molecules, anti-HATF-1 or HRP-1 antibodies, and HATF-1 or HRP-1 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an HATF-1 or HRP-1 protein or nucleic acid molecule.

Stimulation of HATF-1 or HRP-1 activity is desirable in situations in which HATF-1 or HRP-1 is abnormally downregulated and/or in which increased HATF-1 or HRP-1 activity is likely to have a beneficial effect. For example, stimulation of HATF-1 or HRP-1 activity is desirable in situations in which increased HATF-1 or HRP-1 activity is likely to have a beneficial effect, e.g., in the case a proliferative disorder. Likewise, inhibition of HATF-1 or HRP-1 activity is desirable in situations in which HATF-1 or HRP-1 is abnormally upregulated and/or in which decreased HATF-1 or HRP-1 activity is likely to have a beneficial effect, e.g., in the case of a cardiovascular disorder.

In yet another embodiment, the modulatory method of the invention involves contacting a cell with an HATF-1 or HRP-1 molecule or an agent which modulates one or more of the activities of HATF-1 or HRP-1 protein activity associated with the cell. An agent that modulates HATF-1 or HRP-1 protein activity can be an agent as described herein, such as a nucleic acid or a protein, a naturally-occurring target molecule of an HATF-1 or HRP-1 protein (e.g., an HATF-1 or HRP-1 substrate), an HATF-1 or HRP-1 antibody, an HATF-1 or HRP-1 agonist or antagonist, a peptidomimetic of an HATF-1 or HRP-1 agonist or antagonist, or other small molecule. In one embodiment, the agent stimulates one or more HATF-1 or HRP-1 activities. Examples of such stimulatory agents include active HATF-1 or HRP-1 protein and a nucleic acid molecule encoding HATF-1 or HRP-1 that has been introduced into the cell.

3. Pharmacogenomics

The HATF-1 or HRP-1 molecules of the present invention, as well as agents, or modulators which have a stimulatory or inhibitory effect on HATF-1 or HRP-1 activity (e.g., HATF-1 or HRP-1 gene expression) as identified by a screening assay described herein can be administered to individuals to treat (prophylactically or therapeutically) disorders associated with abberant HATF-1 or HRP-1 activity (e.g., cardiovascular disorders). In conjunction with such treatment, pharmnacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an HATF-1 or HRP-1 molecule or HATF-1 or HRP-1 modulator as well as tailoring the dosage and/or therapeutic regimen of treatment with an HATF-1 or HRP-1 molecule or HATF-1 or HRP-1 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11): 983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., an HATF-1 or HRP-1 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C 19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an HATF-1 or HRP-1 molecule or HATF-1 or HRP-1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an HATF-1 or HRP-1 molecule or HATF-1 or HRP-1 modulator, such as a modulator identified by one of the exemplary screening assays described herein.

C. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the HATF-1 or HRP-1 nucleotide sequences, described herein, can be used to map the location of the HATF-1 or HRP-1 genes on a chromosome. The mapping of the HATF-1 or HRP-1 sequences to chromosomes is an important first step in correlating these sequences with genes associated with disease.

Briefly, HATF-1 or HRP-1 genes can be mapped to chromosomes by preparing PCR primers (preferably 15–25 bp in length) from the HATF-1 or HRP-1 nucleotide sequences. Computer analysis of the HATF-1 or HRP-1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the HATF-1 or HRP-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the HATF-1 or HRP-1 nucleotide sequences to design oligonucleotide primers, sublocalization can be achieved with panels of fragments from specific chromosomes. Other mapping strategies which can similarly be used to map an HATF-1 or HRP-1 sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the HATF-1 or HRP-1 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The HATF-1 or HRP-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the HATF-1 or HRP-1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The HATF-1 or HRP-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 3, and/or 5, can comfortably provide positive individual identification with a panel of perhaps 10 to 1,000 primers which each yield a noncoding amplified sequence of 100 bases.

If a panel of reagents from HATF-1 or HRP-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial HATF-1 or HRP-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, 3, and/or 5 are particularly appropriate for this use as greater numbers of polymorphisms occur in the noncoding regions, making it easier to differentiate individuals using this technique. Examples of polynucleotide reagents include the HATF-1 or HRP-L nucleotide sequences or portions thereof, e.g., fragments derived from the noncoding regions of SEQ ID NO:1, 3, and/or 5, having a length of at least 20 bases, preferably at least 30 bases.

The HATF-1 or HRP-1 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such HATF-1 or HRP-1 probes can be used to identify tissue by species and/or by organ type.

In a similar fashion, these reagents, e.g., HATF-1 or HRP-1 primers or probes can be used to screen tissue culture for contamination (i.e. screen for the presence of a mixture of different types of cells in a culture).

D. Screening Assays:

The invention provides a method (also referred to herein as a "screening assay") for identifying modulators, e.g., candidate or test compounds or agents (e.g., peptides, peptidomimetics, small molecules, or other drugs) which bind to HATF-1 or HRP-1 proteins, have a stimulatory or inhibitory effect on, for example, HATF-1 or HRP-1 expression or HATF-1 or HRP-1 activity, or have a stimulatory or inhibitory effect on, for example, the expression or activity of an HATF-1 or HRP-1 substrate.

In one embodiment, the invention provides assays for screening candidate or test compounds which are substrates of an HATF-1 or HRP-1 protein or polypeptide or biologically active portion thereof. In another embodiment, the invention provides assays for screening candidate or test compounds which bind to or modulate the activity of an HATF-1 or HRP-1 protein or polypeptide or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des*. 35 12:145).

Examples of methods for the syntesis of molecular libraries can be found in, for example, DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses an HATF-1 or HRP-1 protein or biologically active portion thereof is contacted with a test compound and the ability of the test compound to modulate HATF-1 or HRP-1 activity is determined. Determining the ability of the test compound to modulate HATF-1 or HRP-1 activity can be accomplished by monitoring, for example, the level of expression of a reporter gene. The cell, for example, can be of mammalian origin. The ability of the test compound to modulate the ability of HATF-1 or HRP-1 to bind to a substrate can also be determined by, for example, coupling the HATF-1 or HRP-1 substrate with a radioisotope or enzymatic label such that binding of the HATF-1 or HRP-1 substrate to HATF-1 or HRP-1 can be determined by detecting the labeled HATF-1 or HRP-1 substrate in a complex. For example, compounds (e.g., HATF-1 or HRP-1 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an HATF-1 or HRP-1 substrate) to interact with HATF-1 or HRP-1 without the labeling of any of the interactants. For example, a microphysiometer can be used to detect the interaction of a compound with HATF-1 or HRP-1 without the labeling of either the compound or the HATF-1 or HRP-1. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and HATF-1 or HRP-1.

In another preferred embodiment, the assay comprises contacting a cell which is responsive to an HATF-1 or HRP-1 protein or biologically active portion thereof, with an HATF-1 or HRP-1 protein or biologically-active portion thereof, to form an assay mixture, contacting the assay mixture with a test compound, and determining the ability of the test compound to modulate the activity of the HATF-1 or HRP-1 protein or biologically active portion thereof, wherein determining the ability of the test compound to modulate the activity of the HATF-1 or HRP-1 protein or biologically active portion thereof comprises determining the ability of the test compound to modulate a biological activity of the HATF-1 or HRP-1-responsive cell (e.g., determining the ability of the test compound to modulate the level of expression of an HATF-1 or HRP-1 regulated gene).

In another embodiment, an assay is a cell-based assay comprising contacting a cell expressing an HATF-1 or HRP-1 target molecule (e.g., an HATF-1 or HRP-1 substrate) with a test compound and determining the ability of the test compound to modulate (e.g. stimulate or inhibit) the activity of the HATF-1 or HRP-1 target molecule. Determining the ability of the test compound to modulate the activity of an HATF-1 or HRP-1 target molecule can be accomplished, for example, by determining the ability of the HATF-1 or HRP-1 protein to bind to or interact with the HATF-1 or HRP-1 target molecule.

Determining the ability of the HATF-1 or HRP-1 protein to bind to or interact with an HATF-1 or HRP-1 target molecule can be accomplished by one of the methods described above for determining direct binding. In a preferred embodiment, determining the ability of the HATF-1 or HRP-1 protein to bind to or interact with an HATF-1 or HRP-1 target molecule can be accomplished by determining the activity of the target molecule. For example, the activity of the target molecule can be determined by detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which an HATF-1 or HRP-1 protein or biologically active portion thereof is contacted with a test compound and the ability of the test compound to bind to the HATF-1 or HRP-1 protein or biologically active portion thereof is determined. Binding of the test compound to the HATF-1 or HRP-1 protein can be determined either directly or indirectly as described above. In a preferred embodiment, the assay includes contacting the HATF-1 or HRP-1 protein or biologically active portion thereof with a known compound which binds HATF-1 or HRP-1 to form an assay mixture, contacting the assay mixture with a test compound, and determining the ability of the test compound to interact with an HATF-1 or HRP-1 protein, wherein determining the ability of the test compound to interact with an HATF-1 or HRP-1 protein comprises determining the ability of the test compound to preferentially bind to HATF-1 or HRP-1 or biologically active portion thereof as compared to the known compound.

In another embodiment, the assay is a cell-free assay in which an HATF-1 or HRP-1 protein or biologically active portion thereof is contacted with a test compound and the ability of the test compound to modulate (e.g., stimulate or inhibit) the activity of the HATF-1 or HRP-1 protein or biologically active portion thereof is determined. Determining the ability of the test compound to modulate the activity of an HATF-1 or HRP-1 protein can be accomplished, for example, by determining the ability of the HATF-1 or HRP-1 protein to bind to an HATF-1 or HRP-1 target molecule by one of the methods described above for determining direct binding. Determining the ability of the HATF-1 or HRP-1 protein to bind to an HATF-1 or HRP-1 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an HATF-1 or HRP-1 protein can be accomplished by determining the ability of the HATF-1 or HRP-1 protein to further modulate the activity of a downstream effector of an HATF-1 or HRP-1 target molecule. For example, the activity of the effector molecule on an appropriate target can be determined or the binding of the effector to an appropriate target can be determined as previously described.

In yet another embodiment, the cell-free assay involves contacting an HATF-1 or HRP-1 protein or biologically active portion thereof with a known compound which binds the HATF-1 or HRP-1 protein to form an assay mixture, contacting the assay mixture with a test compound, and determining the ability of the test compound to interact with the HATF-1 or HRP-1 protein, wherein determining the ability of the test compound to interact with the HATF-1 or HRP-1 protein comprises determining the ability of the HATF-1 or HRP-1 protein to preferentially bind to or modulate the activity of an HATF-1 or HRP-1 target molecule.

In more than one embodiment of the above assay methods, it may be desirable to immobilize either HATF-1 or HRP-1 or its target molecule to facilitate separation of complexed from uncomplexed forms of one or both of the proteins, as well as to accommodate automation of the assay. Binding of a test compound to an HATF-1 or HRP-1 protein, or interaction of an HATF-1 or HRP-1 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/HATF-1 or HRP-1 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or HATF-1 or HRP-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of HATF-1 or HRP-1 binding or activity determined using standard techniques.

Other techniques for immobilizing proteins on matrices can also be used in the screening assays of the invention. For example, either an HATF-1 or HRP-1 protein or an HATF-1 or HRP-1 target molecule can be immobilized utilizing conjugation of biotin and streptavidin. Biotinylated HATF-1 or HRP-1 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidincoated 96 well plates (Pierce Chemical). Alternatively, antibodies reactive with HATF-1 or HRP-1 protein or target molecules but which do not interfere with binding of the HATF-1 or HRP-1 protein to its target molecule can be derivatized to the wells of the plate, and unbound target or HATF-1 or HRP-1 protein trapped in the wells by antibody conjugation. Methods for detecting such complexes, in addition to those described above for the GST-immobilized complexes, include immunodetection of complexes using antibodies reactive with the HATF-1 or HRP-1 protein or target molecule, as well as enzyme-linked assays which rely on detecting an enzymatic activity associated with the HATF-1 or HRP-1 protein or target molecule.

In another embodiment, modulators of HATF-1 or HRP-1 expression are identified in a method wherein a cell is contacted with a candidate compound and the expression of HATF-1 or HRP-1 mRNA or protein in the cell is determined. The level of expression of HATF-1 or HRP-1 mRNA or protein in the presence of the candidate compound is compared to the level of expression of HATF-1 or HRP-1 mRNA or protein in the absence of the candidate compound. The candidate compound can then be identified as a modulator of HATF-1 or HRP-1 expression based on this comparison. For example, when expression of HATF-1 or HRP-1 mRNA or protein is greater (statistically significantly greater) in the presence of the candidate compound than in its absence, the candidate compound is identified as a stimulator of HATF-1 or HRP-1 mRNA or protein expression. Alternatively, when expression of HATF-1 or HRP-1 mRNA or protein is less (statistically significantly less) in the presence of the candidate compound than in its absence, the candidate compound is identified as an inhibitor of HATF-1 or HRP-1 mRNA or protein expression. The level of HATF-1 or HRP-1 mRNA or protein expression in the cells can be determined by methods described herein for detecting HATF-1 or HRP-1 mRNA or protein.

In yet another aspect of the invention, the HATF-1 or HRP-1 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with HATF-1 or HRP-1 ("HATF-1 or HRP-1-binding proteins" or "HATF-1 or HRP-1-bp") and are involved in HATF-1 or HRP-1 activity. Such HATF-1 or HRP-1-binding proteins are also likely to be involved in the propagation of signals by the HATF-1 or HRP-1 proteins or HATF-1 or HRP-1 targets as, for example, downstream elements of an HATF-1 or HRP-1-mediated signaling pathway. Alternatively, such HATF-1 or HRP-1-binding proteins are likely to be HATF-1 or HRP-1 inhibitors. The two-hybrid system is based on the modular nature of most transcription factors, which consist of separable DNA-binding and activation domains. Briefly, the assay utilizes two different DNA constructs. In one construct, the gene that codes for an HATF-1 or HRP-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an HATF-1 or HRP-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the HATF-1 or HRP-1 protein.

This invention further pertains to novel agents identified by the above-described screening assays. Accordingly, it is within the scope of this invention to further use an agent identified as described herein in an appropriate animal model. For example, an agent identified as described herein (e.g., an HATF-1 or HRP-1 modulating agent, an antisense HATF-1 or HRP-1 nucleic acid molecule, an HATF-1 or HRP-1-specific antibody, or an HATF-1 or HRP-1-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

III. Recombinant Expression Vectors and Host Cells

Another aspect of the invention pertains to vectors, preferably expression vectors, containing an HATF-1 or HRP-1 nucleic acid or a portion thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule of the invention in a form suitable for expression of the nucleic acid molecule in a host cell. For example, the recombinant expression vectors can include one or more regulatory sequences, selected on the basis of the host cells to be used for expression, operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described in, for example, Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., HATF-1 or HRP-1 proteins, mutant forms of HATF-1 or HRP-1 proteins, fusion proteins, and the like).

The recombinant expression vectors of the invention can be designed for expression of HATF-1 or HRP-1 proteins in prokaryotic or eukaryotic cells. For example, HATF-1 or HRP-1 proteins can be expressed in bacterial cells such as E. coli, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in HATF-1 or HRP-1 activity assays, (e.g., direct assays or competitive assays described in detail below), or to, for example, generate antibodies specific for HATF-1 or HRP-1 proteins. In a preferred embodiment, an HATF-1 or HRP-1 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

Examples of suitable inducible non-fusion E. coli expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in E. coli is to express the protein in a bacterial host with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111–2118). Such alteration of nucleic acid sequences of the invention can be carried out by standard DNA synthesis techniques.

In another embodiment, the HATF-1 or HRP-1 expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, HATF-1 or HRP-1 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid molecule preferentially in a particular cell type (e.g., tissue-specific regulatory elements are used to express the nucleic acid molecule). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1 985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to HATF-1 or HRP-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an HATF-1 or HRP-1 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an HATF-1 or HRP-1 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an HATF-1 or HRP-1 protein. Accordingly, the invention further provides methods for producing an HATF-1 or HRP-1 protein using the host cells of the invention. In one embodiment, the method comprises culturing the host cell of invention (into which a recombinant expression vector encoding an HATF-1 or HRP-1 protein has been introduced) in a suitable medium such that an HATF-1 or HRP-1 protein is produced. In another embodiment, the method further comprises isolating an HATF-1 or HRP-1 protein from the medium or the host cell.

The host cells of the invention can also be used to produce non-human transgenic animals. For example, in one embodiment, a host cell of the invention is a fertilized oocyte or an embryonic stem cell into which HATF-1 or HRP-1-coding sequences have been introduced. Such host cells can then be used to create non-human transgenic animals in which exogenous HATF-1 or HRP-1 sequences have been introduced into their genome or homologous recombinant animals in which endogenous HATF-1 or HRP-1 sequences have been altered. Such animals are useful for studying the function and/or activity of an HATF-1 or HRP-1 and for identifying and/or evaluating modulators of HATF-1 or HRP-1 activity.

As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous HATF-1 or HRP-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an HATF-1 or HRP-1-encoding nucleic acid into the male pronuclei of a fertilized oocyte, e.g., by microinjection, retroviral infection, and allowing the oocyte to develop in a pseudopregnant female foster animal. The HATF-1 or HRP-1 cDNA sequence of SEQ ID NO:1, 3, and/or 5 can be introduced as a transgene into the genome of a non-human animal. Alternatively, a nonhuman homologue of a human HATF-1 or HRP-1 gene, such as a mouse or rat HATF-1 or HRP-1 gene, can be used as a transgene. Alternatively, an HATF-1 or HRP-1 gene homologue, such as another HATF-1 or HRP-1 family member, can be isolated based on hybridization to the HATF-1 or HRP-1 cDNA sequences of SEQ ID NO:1, 3, and/or 5 (described further in subsection I above) and used as a transgene. Intronic sequences and polyadenylation signals can also be included in the transgene to increase the efficiency of expression of the transgene. A tissue-specific regulatory sequence can be operably linked to an HATF-1 or HRP-1 transgene to direct expression of an HATF-1 or HRP-1 protein to particular cells. Methods for generating transgenic animals via embryo manipulation and microinjection, particularly animals such as mice, are described in, for example, U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an HATF-1 or HRP-1 transgene in its genome and/or expression of HATF-1 or HRP-1 mRNA in tissues or cells of the animals. A transgenic founder animal can then be used to breed additional animals carrying the transgene. Moreover, transgenic animals carrying a transgene encoding an HATF-1 or HRP-1 protein can farther be bred to other transgenic animals carrying other transgenes.

To create a homologous recombinant animal, a vector is prepared which contains at least a portion of an HATF-1 or HRP-1 gene into which a deletion, addition or substitution has been introduced to thereby alter, e.g., functionally disrupt, the HATF-1 or HRP-1 gene. The HATF-1 or HRP-1 gene can be a human gene (e.g., a cDNA isolated by stringent hybridization with the nucleotide sequence of SEQ ID NO:1, 3, and/or 5), but more preferably, is a non-human homologue of a human HATF-1 or HRP-1 gene (e.g., the cDNA of SEQ ID NO:5). For example, a mouse HATF-1 or HRP-1 gene can be used to construct a homologous recombination vector suitable for altering an endogenous HATF-1 or HRP-1 gene in the mouse genome. In a preferred embodiment, the vector is designed such that, upon homologous recombination, the endogenous HATF-1 or HRP-1 gene is functionally disrupted (i.e., no longer encodes a functional protein; also referred to as a "knock out" vector). The vector can also be designed such that, upon homologous recombination, the endogenous HATF-1 or HRP-1 gene is mutated or otherwise altered but still encodes a functional protein (e.g., the upstream regulatory region can be altered to thereby alter the expression of the endogenous HATF-1 or HRP-1 protein). In the homologous recombination vector, the altered portion of the HATF-1 or HRP-1 gene is flanked at its 5' and 3' ends by additional nucleic acid sequence of the HATF-1 or HRP-1 gene to allow for homologous recombination to occur between the exogenous HATF-1 or HRP-1 gene carried by the vector and an endogenous HATF-1 or HRP-1 gene in an embryonic stem cell. The additional flanking HATF-1 or HRP-1 nucleic acid sequence is of sufficient length for successful homologous recombination with the endogenous gene. Typically, several kilobases of flanking DNA (both at the 5' and 3' ends) are included in the vector (see, e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced HATF-1 or HRP-1 gene has homologously recombined with the endogenous HATF-1 or HRP-1 gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO91/01140 by Smithies et al.; WO92/0968 by Zijlstra et al.; and WO93/04169 by Berns et al.

In another embodiment, transgenic non-human animals can be produced which contain selected systems which allow for regulated expression of the transgene. One example of such a system is the credloxP recombinase system of bacteriophage PI. For a description of the crelloxP recombinase system, see, e.g., Lakso et al. (1992) *Proc. Natl. Acad Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO97/07668 and WO97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated bocyte from an animal of the same species from which the quiescent cell is isolated. The reconctructed oocyte is then cultured such that it develops to a morula or a blastocyte and then transferred to a pseudopregnant female foster animal. The offspring borne of this female foster animal will be clones of the animal from which the cell, e.g., the somatic cell, is isolated.

IV. Pharmaceutical Compositions

The HATF-1 or HRP-1 nucleic acid molecules, HATF-1 or HRP-1 proteins, and anti-HATF-1 or HRP-1 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monstearate and gelatin.

Sterile injectable solutions can be prepared by incorporating the active compound (e.g., an HATF-1 or HRP-1 nucleic acid molecule an HATF-1 or HRP-1 protein, or anti-HATF-1 or HRP-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdernal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within-this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Isolated HATF-1 and HRP-1 Proteins and Anti-HATF-1 and Anti-HRP-1 Antibodies

One aspect of the invention pertains to isolated HATF-1 and HRP-1 proteins, and biologically active portions thereof, as well as polypeptide fragments suitable for use as immunogens to raise anti-HATF-1 and anti-HRP-1 antibodies. In one embodiment, native HATF-1 and HRP-1 proteins can be isolated from cells or tissue sources by an appropriate purification scheme using standard protein purification techniques. In another embodiment, HATF-1 and HRP-1 proteins are produced by recombinant DNA techniques. Alternative to recombinant expression, an HATF-1 and HRP-1 protein or polypeptide can be synthesized chemically using standard peptide synthesis techniques.

An "isolated" or "purified" protein or biologically active portion thereof is substantially free of cellular material or other contaminating proteins from the cell or tissue source from which the HATF-1 and HRP-1 protein is derived, or substantially free from chemical precursors or other chemicals when chemically synthesized. The language "substantially free of cellular material" includes preparations of HATF-1 and HRP-1 protein in which the protein is separated from cellular components of the cells from which it is isolated or recombinantly produced. In one embodiment, the language "substantially free of cellular material" includes preparations of HATF-1 and HRP-1 protein having less than about 30% (by dry weight) of non-HATF-1 and non-HRP-1 protein (also referred to herein as a "contaminating protein"), more preferably less than about 20% of non-HATF-1 and non-HRP-1 protein, still more preferably less than about 10% of non-HATF-1 and non-HRP-1 protein, and most preferably less than about 5% non-HATF-1 and non-HRP-1 protein. When the HATF-1 and HRP-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of HATF-1 and HRP-1 protein in which the protein is separated from chemical precursors or other chemicals which are involved in the synthesis of the protein. In one embodiment, the language "substantially free of chemical precursors or other chemicals"includes preparations of HATF-1 and HRP-1 protein having less than about 30% (by dry weight) of chemical precursors or non-HATF-1 and non-HRP-1 chemicals, more preferably less than about 20% chemical precursors or non-HATF-1 and non-HRP-1 chemicals, still more preferably less than about 10% chemical precursors or non-HATF-1 and non-HRP-1 chemicals, and most preferably less than about 5% chemical precursors or non-HATF-1 and non-HRP-1 chemicals.

Biologically active portions of an HATF-1 and HRP-1 protein include peptides comprising amino acid sequences sufficiently homologous to or derived from the amino acid sequence of the HATF-1 and HRP-1 protein, e.g., the amino acid sequence shown in SEQ ID NO:2 or 4, which include less amino acids than the full length HATF-1 and HRP-1 proteins, and exhibit at least one activity of an HATF-1 and HRP-1 protein. Typically, biologically active portions comprise a domain or motif with at least one activity of the HATF-1 and HRP-1 protein. A biologically active portion of an HATF-1 and HRP-1 protein can be a polypeptide which is, for example, 10, 20, 25, 30, 40, 50, 100, 250, 200, 250, or more amino acids in length.

In a preferred embodiment, the HATF-1 and HRP-1 protein has an amino acid sequence shown in SEQ ID NO:2 or 4. Another embodiments, the HATF-1 and HRP-1 protein is substantially homologous to SEQ ID NO:2 or 4, and retains the functional activity of the protein of SEQ ID NO:2 or 4, yet differs in amino acid sequence due to natural allelic variation or mutagenesis, as described in detail in subsection I above. Accordingly, in another embodiment, the HATF-1 or HRP-1 protein is a protein which comprises an amino acid sequence at least about 40%, 45%, 50%, 55%, 60%, 65%, 70%, 75%, 80%, 85%, 90%, 95% 98% or more homologous to SEQ ID NO:2 or 4.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence having 177 amino acid residues, to the HATF-1 or HRP-1 amino acid sequence of SEQ ID NO:2 or 4, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

The comparison of sequences and determination of percent homology between two sequences can be accomplished using a mathematical algorithim. A preferred, non-limiting example of a mathematical algorithim utilized for the comparison of sequences is the algorithm of Karlin and Altschul (1990) *Proc. Natl. Acad. Sci. USA* 87:2264–68, modified as in Karlin and Altschul (1993) *Proc. Natl. Acad. Sci. USA* 90:5873–77. Such an algorithm is incorporated into the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to HATF-1 and HRP-1 nucleic acid molecules of the invention. BLAST protein searches can be performed with the XBLAST program, score=50, wordlength=3 to obtain amino acid sequences homologous to HATF-1 and HRP-1 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithims for sequence analysis are known in the art, and include ADVANCE and ADAM. described in Torelli and Robotti (1994) *Comput. Appl. Biosci.* 10:3–5; and FASTA, described in Pearson and Lipman (1988) *P.N.A.S.* 85:2444–8.

In another preferred embodiment, the percent homology between two amino acid sequences can be accomplished using the GAP program in the GCG software package (available at http://www.gcg.com), using either a Blossom 62 matrix or a PAM250 matrix, and a gap weight of 12, 10, 8, 6, or 4 and a length weight of 2, 3, or 4. In yet another preferred embodiment, the percent homology between two nucleic acid sequences can be accomplished using the GAP program in the GCG software package (available at http:H/www.gcg.com), using a gap weight of 50 and a length weight of 3.

The invention also provides HATF-1 and HRP-1 chimeric or fusion proteins. As used herein, an HATF-1 or HRP-1 "chimeric protein" or "fusion protein" comprises an RATF-1 or HRP-1 polypeptide operatively linked to a non-HATF-1 or a non-HRP-1 polypeptide. An "HATF-1" or "HRP-1 polypeptide" refers to a polypeptide having an amino acid sequence corresponding to HATF-1 or HRP-1, whereas a "non-HATF-1" or "non-HRP-1" polypeptide refers to a polypeptide having an amino acid sequence corresponding to a protein which is not substantially homologous to the HATF-1 or HRP-1 protein, e.g., a protein which is different from the HATF-1 or HRP-1 protein and which is derived from the same or a different organism. Within an HATF-1 or HRP-1 fusion protein the HATF-1 or HRP-1 polypeptide can correspond to all or a portion of an HATF-1 or HRP-1 protein. In a preferred embodiment, an HATF-1 or HRP-1 fuision protein comprises at least one biologically active portion of an HATF-1 or HRP-1 protein. In another preferred embodiment, an HATF-1 or HRP-1 fusion protein comprises at least two biologically active portions of an HATF-1 or HRP-1 protein. Within the fusion protein, the term "operatively linked" is intended to indicate that the HATF-1 or HRP-1 polypeptide and the non-HATF-1 or non-HRP-1 polypeptide are fused in-frame to each other. The non-HATF-1 or non-HRP-1 polypeptide can be fused to the N-terminus or C-terminus of the HATF-1 or HRP-1 polypeptide.

For example, in one embodiment, the fusion protein is a GST-HATF-1 or GST-HRP-1 fusion protein in which the HATF-1 or HRP-1 sequences are fused to the C-termninus of the GST sequences. Such fusion proteins can facilitate the purification of recombinant HATF-1 or HRP-1.

In another embodiment, the fusion protein is an HATF-1 or HRP-1 protein containing a heterologous signal sequence at its N-terminus. In certain host cells (e.g., mammalian host cells), expression and/or secretion of HATF-1 or HRP-1 can be increased through use of a heterologous signal sequence.

The HATF-1 or HRP-1 fusion proteins of the invention can be incorporated into pharmaceutical compositions and administered to a subject in vivo. The HATF-1 or HRP-1 fusion proteins can be used to affect the bioavailability of an HATF-1 or HRP-1 substrate. Use of HATF-1 or HRP-1 fusion proteins may be useful therapeutically for the treatment of cardiovascular disorders, e.g., hypertension.

Moreover, the HATF-1 or HRP-1-fusion proteins of the invention can be used as immunogens to produce anti-HATF-1 or anti-HRP-1 antibodies in a subject, to purify HATF-1 or HRP-1 ligands and in screening assays to identify molecules which inhibit the interaction of HATF-1 or HRP-1 with an HATF-1 or HRP-1 substrate.

Preferably, an HATF-1 or HRP-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termnini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An HATF-1 or HRP-1-encoding nucleic acid can be cloned into such an expression vector such that the fusion moiety is linked in-frame to the HATF-1 or HRP-1 protein.

The present invention also pertains to variants of the HATF-1 or HRP-1 proteins which function as either HATF-1 or HRP-1 agonists (mimetics) or as HATF-1 or HRP-1 antagonists. Variants of the HATF-1 or HRP-1 proteins can be generated by mutagenesis, e.g., discrete point mutation or truncation of an HATF-1 or HRP-1 protein. An agonist of the HATF-1 or HRP-1 proteins can retain substantially the same, or a subset, of the biological activities of the naturally occurring form of an HATF-1 or HRP-1 protein. An antagonist of an HATF-1 or HRP-1 protein can inhibit one or more of the activities of the naturally occurring form of the HATF-1 or HRP-1 protein by, for example, competitively modulating a cardiovascular disorder-associated activity of an HATF-1 or HRP-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the HATF-1 or HRP-1 protein.

In one embodiment, variants of an HATF-1 or HRP-1 protein which function as either HATF-1 or HRP-1 agonists (mimetics) or as HATF-1 or HRP-1 antagonists can be identified by screening combinatorial libraries of mutants, e.g., truncation mutants, of an HATF-1 or HRP-1 protein for HATF-1 or HRP-1 protein agonist or antagonist activity. In one embodiment, a variegated library of HATF-1 or HRP-1 variants is generated by combinatorial mutagenesis at the nucleic acid level and is encoded by a variegated gene library. A variegated library of HATF-1 or HRP-1 variants can be produced by, for example, enzymatically ligating a mixture of synthetic oligonucleotides into gene sequences such that a degenerate set of potential HATF-1 or HRP-1 sequences is expressible as individual polypeptides, or alternatively, as a set of larger fulsion proteins (e.g., for phage display) containing the set of HATF-1 or HRP-1 sequences therein. There are a variety of methods which can be used to produce libraries of potential HATF-1 or HRP-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential HATF-1 or HRP-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ice et al. (1 983) *Nucleic Acid Res.* 11:477.

In addition, libraries of fragments of an HATF-1 or HRP-1 protein coding sequence can be used to generate a variegated population of HATF-1 or HRP-1 fragments for screening and subsequent selection of variants of an HATF-1I or HRP-1 protein. In one embodiment, a library of coding sequence fragments can be generated by treating a double stranded PCR fragment of an HATF-1 or HRP-1 coding sequence with a nuclease under conditions wherein nicking occurs only about once per molecule, denaturing the double stranded DNA, reentering the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal, C-terminal and internal fragments of various sizes of the HATF-1 or HRP-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of HATF-1 or HRP-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify HATF-1 or HRP-1 variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated HATF-1 or HRP-1 library. For example, a library of expression vectors can be transfected into a cell line which ordinarily synthesizes HATF-1 or HRP-1. The transfected cells can then be cultured such that HATF-1 or HRP-1 and a particular mutant HATF-1 or HRP-1 are expressed and the effect of expression of the mutant on HATF-1 or HRP-1 activity in the cells can be detected, e.g., by any of a number of enzymatic assays or by monitoring cell survival, e.g., by monitoring cellular morphological features such as chromatin condensation. Plasmid DNA can then be recovered from the cells which score for inhibition, or alternatively, potentiation of HATF-1 or HRP-1 activity, and the individual clones further characterized.

In another embodiment, a variegated HATF-1 or HRP-1 library can be analyzed by determining the ability of the HATF-1 or HRP-1 variants to modulate the development of hypertension in a tissue which normally expresses HATF-1 or HRP-1.

An isolated HATF-1 or HRP-1 protein, or a portion or fragment thereof, can be used as an immunogen to generate antibodies that bind HATF-1 or HRP-1 using standard techniques for polyclonal and monoclonal antibody preparation. A full-length HATF-1 or HRP-1 protein or antigenic peptide fragments of HATF-1 or HRP-1 can be used as immunogens. An antigenic peptide of HATF-1 or HRP-1 comprises at least 8 amino acid residues of the amino acid sequence shown in SEQ ID NO:2 or 4 and encompasses an epitope of HATF-1 or HRP-1 such that an antibody raised against the peptide forms a specific immune complex with HATF-1 or HRP-1. Preferably, the antigenic peptide comprises at least 10 amino acid residues, more preferably at least 15 amino acid residues, even more preferably at least amino acid residues, and most preferably at least 30 amino acid residues.

Preferred epitopes encompassed by the antigenic peptide are regions of HATF-1 or HRP-1 that are located on the surface of the protein, e.g., hydrophilic regions.

An HATF-1 or HRP-1 immunogen typically is used to prepare antibodies by immunizing a suitable subject, (e.g., rabbit, goat, mouse or other mammal) with the immunogen. An appropriate immunogenic preparation can contain, for example, recombinantly expressed HATF-1 or HRP-1 protein or a chemically synthesized HATF-1 or HRP-1 polypeptide. The preparation can further include an adjuvant, such as Freund's complete or incomplete adjuvant, or similar immnunostimulatory agent. Immunization of a suitable subject with an immunogenic HATF-1 or HRP-1 preparation induces a polyclonal anti-HATF-1 or anti-HRP-1 antibody response.

Accordingly, another aspect of the invention pertains to anti-HATF-1 or anti-HRP-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as HATF-1 or HRP-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind HATF-1 or HRP-1. The term "monoclonal antibody" or monoclonal antibody composition", as used herein, refers to a population of antibody molecules that contain only one species of an antigen binding site capable of immunoreacting with a particular epitope of HATF-1 or HRP-1. A monoclonal antibody composition, thus, typically displays a single binding affinity for a particular HATF-1 or HRP-1 protein with which it immunoreacts.

Polyclonal anti-HATF-1 or anti-HRP-1 antibodies can be prepared as described above by immunizing a suitable subject with an HATF-1 or HRP-1 immunogen. The anti-HATF-1 or anti-HRP-1 antibody titer in the immunized subject can be monitored over time by standard techniques, such as with an enzyme linked immunosorbent assay (ELISA) using immobilized HATF-1 or HRP-1. If desired, the antibody molecules directed against HATF-1 or HRP-1 can be isolated from the mammal (e.g., from the blood) and further purified by well known techniques, such as protein A chromatography to obtain the IgG fraction. At an appropriate time after immunization, e.g., when the anti-HATF-1 or anti-HRP-1 antibody titers are the highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (198 1) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an HATF-1 or HRP-1 immunogen as described above, and the culture supernatants of the resulting hybridoma cells are screened to identify a hybridoma producing a monoclonal antibody that binds HATF-1 or HRP-1.

Any of the many well known protocols used for fusing lymphocytes and immortalized cell lines can be applied for the purpose of generating an anti-HATF-1 or anti-HRP-1 monoclonal antibody (see, e.g., G. Galfre et al. (1977) *Nature* 266:55052; Gefter et al. *Somatic Cell Genet.*, cited supra; Lerner, *Yale J. Biol. Med*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind HATF-1 or HRP-1, e.g., using a standard ELISA assay.

Alternative to preparing monoclonal antibody-secreting hybridomas, a monoclonal anti-HATF-1 or anti HRP-1 antibody can be identified and isolated by screening a recombinant combinatorial immunoglobulin library (e.g., an antibody phage display library) with HATF-1 or HRP-1 to thereby isolate immunoglobulin library members that bind HATF-1 or HRP-1. Kits for generating and screening phage display libraries are commercially available (e.g., the Pharmacia *Recombinant Phage Antibody System*, Catalog No. 27-9400-01; and the Stratagene SurfZAp™ Phage Display Kit, Catalog No. 240612). Additionally, examples of methods and reagents particularly amenable for use in generating and screening antibody display library can be found in, for example, Ladner et at. U.S. Pat. No. 5,223,409; Kang et al. PCT International Publication No. WO92/18619; Dower et al. PCT International Publication No. WO91/17271; Winter et al. PCT International Publication WO92/20791; Markland et al. PCT International Publication No. WO 92/15679; Breitling et al. PCT International Publication WO93/01288; McCafferty et al. PCT International Publication No. WO92/01047; Garrard et al. PCT International Publication No. WO92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-HATF-1 or anti-HRP-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-HATF-1 or anti-HRP-1 antibody (e.g., monoclonal antibody) can be used to isolate HATF-1 or HRP-1 by standard techniques, such as affinity chromatography or immunoprecipitation. An anti-HATF-1 or anti-HRP-1 antibody can facilitate the purification of natural HATF-1 or HRP-1 from cells and of recombinantly produced HATF-1 or HRP-1 expressed in host cells. Moreover, an anti-HATF-1 or anti-HRP-1 antibody can be used to detect HATF-1 or HRP-1 protein (e.g., in a cellular lysate or cell supernatant) in order to evaluate the abundance and pattern of expression of the HATF-1 or HRP-1 protein. Anti-HATF-1 or anti-HRP-1 antibodies can be used diagnostically to monitor protein levels in tissue as part of a clinical testing procedure to, for example, determine the efficacy of a given treatment regimen. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidinibiotin and avidinibiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{25}$I, $^{131}$I, $^{35}$S or $^{3}$H.

This invention is further illustrated by the following examples which should not be construed as limiting. The contents of all references, patents and published patent applications cited throughout this application, including the figures and the Sequence Listing, are incorporated herein by reference.

EXAMPLES

The following material and methods were used in the Examples.

Cell Culture

Mesangial cells from SHR and WKY rats were isolated and cultured as described in Abboud H. et al. (1987) *J. Clin. Invest.* 80:675–83. Rat mesangial cells were routinely grown in 10% fetal bovine serum (FBS) (Hyclone, Logan, UT) Dulbecco's modified Eagle's media (DMEM) (Gibco BRL, Gaithersburg, Md.) and used between passages four and ten. SHR and WKY rat cerebrovascular endothelial cells were isolated and cultured as described by Herman, et al. (1987) *Tissue and Cell* 20(1):1–12. Rat endothelial cells were routinely grown in 10% FBS and used between passages three and seven.

Isolation of Newborn Rat Brains

Pregnant hypertensive and norrnotensive rats were obtained from a commercial supplier (Taconic, Germantown, N.Y.) and housed at the Department of Laboratory Animal Medicine, Tufts University. Systolic blood pressure measurements were taken on the post-partum hypertensive and normotensive mothers as previously described and were in agreement with previously published results. Between 3–10 days post-partum, rat pups were sacrificed by decapitation on ice. Brains were immediately removed, rinsed with sterile PBS, and snap-frozen in liquid nitrogen prior to RNA isolation over CsCI cushions.

RNA Isolation

Total cellular RNA was extracted from cells and tissues minor modifications of the guanidine isothiocyanate/cesium chloride centrifugation method described in Chirgwin et al. (1979) *Biochemistry* 18:5294–9. Briefly, confluent cultures were washed 3 times in 1×PBS, then lysed in guanidine isothiocyanate (GT) buffer (GT buffer is guanidine isothiocyanate, citric acid, N-lauroyl sarcosine, EDTA and β-mercaptoethanol). Cellular lysates were drawn through bent 21 gauge needles to shear chromosomal DNA and spun through cesium chloride cushions at 24,000 rpm for approximately 14 hours. RNA pellets were resuspended in water, phenol:chloroform (1:1) extracted, and precipitated with ethanol, then resuspended in water and stored at −70° C. until used.

For tissue samples, rat pup brains were isolated as described above and pulverized to a fine powder with RNase-free instruments. Total cellular RNA was then extracted with GT buffer, with at least 15 ml of buffer used per 1.0 g tissue (wet weight). Cellular lysates were then processed as described above.

Differential mRNA Display RT-PCR

Differential mRNA display RT-PCR was performed essentially as described, in Liang P. et al. (1 992) *Science* 257:967–971 and Bhandari B. et al. (1994) *Biochemical Journal* 297:385–8 with minor modifications. Typically, 20 μg of total RNA obtained from day 10 post-partum SHR and WKY brains (n>20) were treated with DNase I (Gibco BRL) in the presence of a placental RNase inhibitor (Gibco BRL, Gaithersburg, Md.) in 1×PCR buffer for 30 minutes at 37° C. to remove residual contaminating genomic DNA. DNase-treated RNA from control and experimental conditions were separately reverse transcribed using SuperScriptII reverse transcriptase (Gibco BRL, Gaithersburg, Md.) in duplicate using either $T_{12}MA$, $T_{12}MG$, or T12MC oligonucleotides (where M indicates equimolar amounts G, A, and C). The reverse transcription reaction, containing 400–800 ng DNase-treated RNA, 1×First Strand buffer, 10 mM dithiothreitol, 20 μM each of dATP, dCTP, dTTP, and dGTP, and 0.5 μM $T_{12}MX$ poly (A)-anchored primer, was first heated at 65° C. for 5 minutes, cooled to 37° C. for 10 minutes, at which point the reverse transcriptase (200 units)

was added and the reaction continued for 1 hour at 37° C. The enzyme was inactivated at 95° C. for 5 minutes. PCR was performed in 0.2 ml thin walled tubes containing 0.1 volume of the cDNA produced above, 1×PCR buffer containing 1.5 mM MgCl, 2 μM each of dCTP, dTTP, and dGTP, 1 μM dATP, 10 μCi of $^{35}$S-dATP (1 Ci=37 GBq) (New England Nuclear, Boston, Mass.), 0.5 μM of the respective $T_{12}$MX primer, 1 μM of a 10 mer of arbitrary sequence (Operon, Alameda, Calif.), and 1 unit of Taq polymerase (Gibco BRL, Gaithersburg, Md.) for 40 cycles of 94° C. for 30 seconds, 42° C. for 2 minutes, 72° C. for 30 seconds, followed by a final extension at 72° C. for 10 minutes, in a Perkin Elmer 9600 or 40 cycles of 94° C. for 5 seconds, 92° C. for 30 seconds, 40° C. for 2 minutes, 72° C. for 30 seconds, followed by a for 5 extension at 72° C. for 10 minutes in a thermal cycler (PTC-100; M J Research, Watertown, Mass.).

Differential mRNA Display Gel Electrophoresis

The labeled PCR products were combined with display loading buffer (50% formamide, 0.01% xylene cyanol, 0.01% bromophenol blue, 1 mM EDTA) in a ratio of 7:4, heated to 85° C. for 2 minutes, then subjected to electrophoresis through a 6% polyacrylamide sequencing gel (National Diagnostics, Atlanta, Ga.) at 65W constant current for 2.5 to 3 hours. The gel was transferred to blotting paper, dried without fixation, marked in the corners with $^{35}$S-dATP-labelled black ink, and exposed to XAR-5 or Biomax (Eastman Kodak, Rochester, N.Y.) film overnight to 3 days. Bands of differing intensity indicated differential gene expression between conditions, which migrate to identical positions in the sequencing gel.

Purification of cDNA Fragments from Differential mRNA Display Gels $^{35}$S-labeled cDNAs appearing as bands on autoradiographic film and representing differentially expressed mRNAs were identified and excised by cutting through the film. The dried gel together with the blotting paper backing was placed in clean microf-uge tubes. The DNA was eluted from the gel slice in 100 μl of 100° C. $H_2O$. Re-amplification using display primers yielded sufficient amounts of DNA for subsequent manipulations. PCR products were cloned into plasmid vectors using SureClone (Pharmacia, Milwaukee, Wis.) and sequenced using the Sequenase 7-deaza-dGTP Sequencing kit (Amersham, Cleveland, Ohio).

Northern Analysis

Total cellular RNA isolated as described previously, was quantified by absorbance at 260 nm and run on a 1.2% gel containing 2.2M formaldehyde in a buffer of 1×TBE (1×TBE is 90 mM Tris borate and 2 mM EDTA) for 2.5 to 3 hours at 80V with constant recirculation of the buffer. 15 μg of total cellular RNA from each condition was used. Gels were stained with ethidium bromide, and Northern blotting was performed by capillary transfer to Nytran membranes (Schleicher&Schuell, Keene, N.H.) in 10×SSC (1×SSC in 0.15M sodium chloride, 0.015M sodium citrate, pH 7.0) as described. RNA was crosslinked to the membranes using a UV-crosslinker and prehybridized at 42° C. for 4 hours in 50% de-ionized formamide, 5×SSPE, 5×Denhardt's solution, 1% sodium dodecyl sulfate, 10% dextran sulfate, and 100 μg/ml salmon sperm DNA (Sigma, St. Louis, Mo.). The blots were then hybridized at 42° C. for more than 16 hours in 50% de-ionized formamide, 5×SSPE, 1×Denhardt's solution, 1% sodium dodecyl sulfate, 10% dextran sulfate, and 100 μg/ml poly (A) with $^{32}$P-labelled cDNAs. After hybridization the blots were washed twice at 65° C. for 5 minutes with 2×SSPE and 1% SDS; followed by one washing for 5 minutes with 0.1×SSPE at 65° C. Detection of specific hybridization was performed using a Phosphorimager (Molecular Dynamics, Sunnyvale, Calif.). Relative signal intensity was determnined using an IS-1000 digital imager (Alpha-Innotech, Palo Alto, Calif.). The size (in kilobases) of detected mRNAs was determined by comparison with 28S and 18S ribosomal RNA migration and an RNA ladder.

Production of cDNA Probes

Asymmetric PCR was performed essentially as described to generate $^{32}$P-labeled cDNA probes. PCR reactions were performed in 0.2 ml thin walled tubes containing 1×PCR buffer containing 1.5 mM magnesium chloride, 200 μM dGTP, 200 μM DATP, 200 μM dTfP, 8 μM dCTP, 50 μCi 32P-dCTP, 50 pmol oligonucleotide primer, 1 μg linearized template DNA, and 2.5U Taq polymerase (Gibco BRL, Gaithersburg, Md.). Reaction conditions were as follows: 40 cycles of 94° C. for 1 minute, 50° C. for 2 minutes and 72° C. for 2 minutes. PCR products were purified through push columns (Stratagene, La Jolla, Calif.) and added to Northern blots at 1×10$^6$ cpm/ml.

Extension of cDNA fragments using Rapid Amplification of cDNA Ends (RACE)

Extension of the cloned cDNA fragments by RACE was performed essentially as described by the manufacturer (Gibco BRL, Gaithersburg, Md.). 1 μg of total cellular RNA was reverse transcribed using an oligonucleotide primer specific for HATF1, after which template RNA was degraded with RNaseH. cDNAs were tailed with dCTP and terminal deoxytransferase (TdT) and subjected to two consecutive rounds of PCR using nested primers specific for HATF 1 and the provided anchor primer. PCR products were inserted into commercial cloning vectors and sequenced. Primer sequences for RACE are: Round 1: and Round 2: RT-AAGTGCTGCATTTGTGGCAG (SEQ ID NO:6); PCR1-GCTTCTTAGTGGGCACATTC(SEQ ID NO:7); PCR2-GAATGCCGGTGGACATGGAA (SEQ ID NO:8) Round 3: RT-GTCTTCTTGACATCTCTCTTG (SEQ ID NO:9); PCR1-TTACGGACCTCTTTGCCATG (SEQ ID NO:10); PCR2-GTAAAGTTTGACTTCCACCG (SEQ ID NO:11).

Generation of Anti-HATF-1 Polyclonal Antibodies

Polyclonal antibodies were generated in rabbits against a synthetic polypeptide derived from the deduced HATF-1 amino acid sequence as previously described using TiterMax Gold (CytRx, Norcross, GA) as adjuvant. The amino acid sequence used was E-L-S-G-K-K-P-L-D-N-P-S-H-E-S-S-M (SEQ ID NO:12), which corresponds to a region of the protein lacking zinc finger motifs or homology to any known proteins described in available databases. 750 μg of emulsified peptide was delivered intradermally and 750 μg intramuscularly. Four weeks later a single 750 μg boost was delivered intramuscularly; bleeds were taken from ear veins seven days after each boost as described in Herman I. M. et al. (1979) *J. Cell Biol.* 80(3):509–20.

Western Blot Analysis

Tissue Samples

SHR tissue lysates were generated from pre-hypertensive and hypertensive SHR. A 6 week old male (mean systolic blood pressure of 103 mm Hg) and a 14 week old male (mean systolic blood pressure of 185 mm Hg) (Taconic, Tarrytown, N.Y.) were sacrificed, tissues were isolated and snap-frozen in liquid nitrogen then lyophilized. Small fragments of dehydrated tissue were solubilized in hot SDS sample buffer (4% SDS, 20% beta-mercaptoethanol 20% gylcerol, 125 mM Tris), clarified by centrifugation and subjected to polyacrylamide gel electrophoresis (PAGE) under denaturing conditions and transferred to Protran solid membranes (Schleicher&Schuell, Keene, N.H.).

Mesangial Cells

Whole cell lysates from SHR cultured mesangial cells were generated in SDS sample (as above) and subjected to PAGE (see above). Blots were blocked for 1 hour at room temperature in TBST containing 5% fat-free milk. Irmnunized rabbit serum (see above) was added at a dilution of 1:200 in 2.5% fat-free milk in TBST for 1 hour at room temperature in a humidified chamber. Blots were washed extensively in TBST then incubated for 1 hour in a humidified chamber using a 1:3000 dilution of goat anti-rabbit IgG conjugated to HRP. Detection was performed by ECL as described by the supplier (Super Signal, Pierce, Rockford, Ill.). Pre-immune serum from the same rabbit was used as a control.

Immunofluorescence

Localization of HATF-1 protein in SHR-derived cultured mesangial cells was performed essentially as described previously. SHR mesangial cells plated on multiwell chamber slides (Becton Dickenson, Franklin Lakes, N.J.) were fixed in 4% paraformaldehyde/DMEM for 5 minutes at room temperature, washed against PBS, permeabilized in triton-containing lysis solution (0.1% Triton X-100, 50 mM HEPES, 50 mM PIPES, 1 mM $MgCl_2$, 0.1 mM EGTA, 75 mM KCl), then washed again in PBS. Primary antibody incubation used a 1:200 to 1:800 dilution of immunized rabbit serum (see above) in PBS for 1 hour at room temperature then washed against PBS. Secondary antibody incubation used a 1:200 dilution of goat anti-rabbit IgG conjugated to rhodamine (Jackson Immunoresearch, West Grove, Pa.) for 1 hour at room temperature then washed against PBS, and mounted in 90%glycerol/10%PBS and observed using an inverted fluorescence microscope. Pre-immune serum from the same rabbit was used as a control.

EXAMPLE 1

Isolation of a Hypertension-associated cDNA Using Differential mRNA Display

Figure 1:
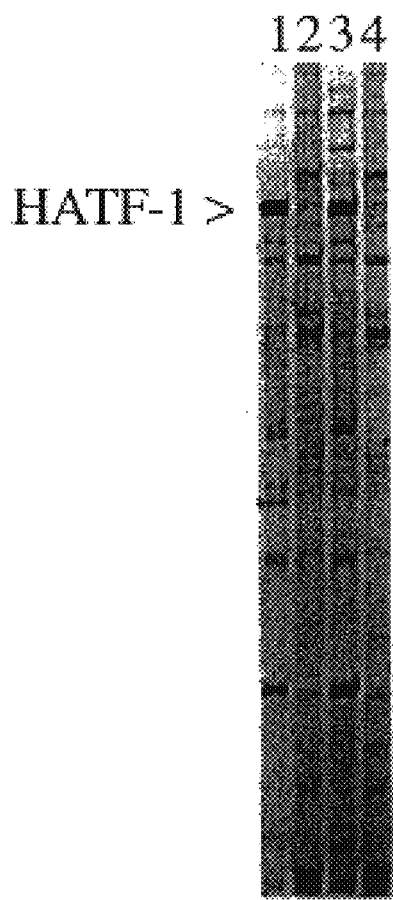
FIG. 1 is a depiction of a gel demonstrating the isolation of a hypertension-associated cDNA using mRNA display of a hypertensive (SHR, lane1) and nonmotensive (WKY, lane 2) neonatal rat brain. The arrow indicates the location of a 400 basepair cDNA that is in 8-fold greater abundance in SHR versus WKY. Lanes 3 (SHR) and 4 (WKY) are duplicate amplifications of lanes 1 and 2.
Figure 2:
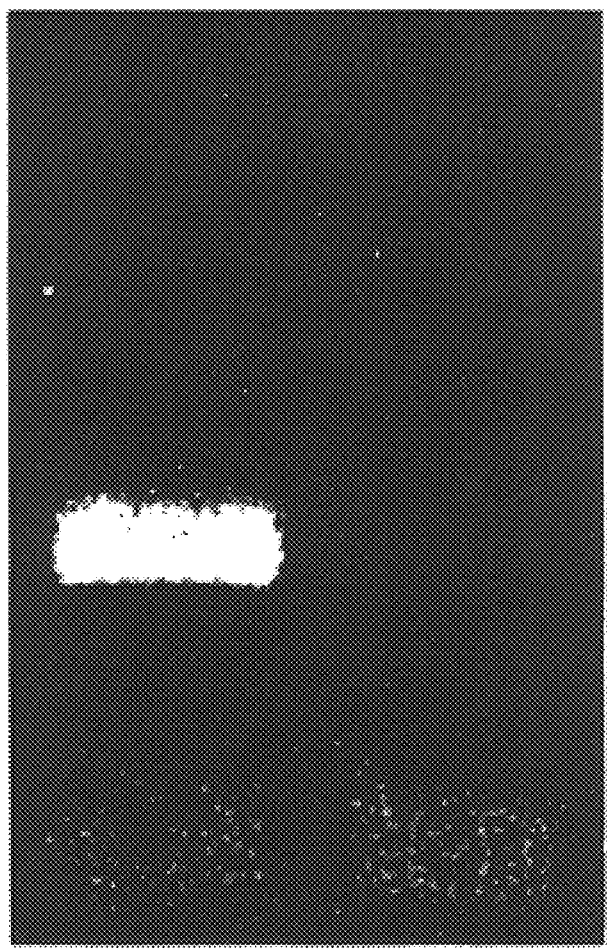
FIG. 2 depicts a gel demonstrating the results from a reverse transcription-polymerase chain reaction amplification of a hypertension-specific cDNA from SHR and WKY neonatal rat brain RNAs. Gene specific primers were used to amplify a 313 base pair cDNA from SHR (lane 1) and WKY (lane 2) that is found at 10-fold higher levels in SHR. Reverse transcribed cDNAs were diluted 1:100 prior to PCR. As a negative control a PCR reaction was performed without a reverse transcription product.

Differential mRNA display was used to visualize differences in the patterns of gene expression in hypertensive (SLIR) and normotensive control (WKY) neonatal rat brains. Total RNA from newborn rat brains was purified and subjected to reverse transcription-polymerase chain reaction (RT-PCR) using various primer combinations as described in Liang and Pardee (1992) Science 257:967–71. One primer combination presented a number of differences in the banding pattern of SHR versus WKY (see FIG. 1). Among several cDNA fragments cloned by this approach, a 400 bp cDNA clone (FIG. 1, Arrow) was determined by Densitometric analysis to be expressed in SHR at levels 8-fold higher than in normotensive controls. This cDNA fragment was gel-purified and re-amplified using PCR conditions identical to the initial display. Gene-specific primers designed against this cDNA were used to specifically amplify the single cDNA, and confirm that the cloned cDNA represented a differentially expressed mRNA (see FIG. 2). Nucleic acid analysis of the cDNA fragment indicated the presence of several consensus C2H2 zinc finger DNA binding domains in the predicted amino acid sequence (Table I).

EXAMPLE 2

Sequence Structure of a Novel mRNA Reveals Consensus DNA-binding Elements

The fiil-length cDNA from the display clone was obtained by cDNA extension methods (5'- and 3'-rapid amplification of cDNA ends [RACE]) and by screening a cDNA library prepared from neonatal SHR brain RNA as described above. Translation of the determined nucleotide sequence revealed an open reading frame of more than 2500 base pairs encoding a protein of 415 amino acids with a predicted molecular mass of 47.7 kDa (see FIG. 3). Although this transcript is novel, comparison of its sequence with published sequences reveals 40–56% identity within regions that are homologous with a number of members of this H-type zinc finger DNA-binding transcription factor gene family (Table 1).

The sequence identity was highest in regions containing the DNA-binding motifs, and in particular, within the consensus matched pairing of cysteines and histidines along with the phenylalanine found at position 8 in the zinc finger region of transcription factors (Table I).

TABLE 1

HATF-1 homology with known zinc-finger proteins

| | | |
|---|---|---|
| HATF-1 94 EKPFWC...QECGKTFTRKR S L L D HKG I HSGER RFKCNL......C E KS F | | (SEQ ID NO:13) |
| WT-I 380 VKPFQC...K T C Q R K F S R S D H L KT HT RT HT GEK PFS CRW PS CQKKF | | (SEQ ID:14) |
| NK-10 303 EKPYQC...SLCGKAFQRSS S L VQ HQ RI HTGEK PYRCNL.....C GRS F | | (SEQ ID NO:15) |
| HF-10 323 EKCYEC...NECGKTFTRSS N LIV HQ RI HTGEK PFACND.....CG KA F | | (SEQ ID NO:16) |
| KID-1 241 EKPYVC...KE CGKAFTLSTS L YK H L RTHTVEK SYRCKE.....C G KS F | | (SEQ ID NO:17) |
| YY-I 350 EKPF Q C TFEGCGKRFS LDPNL RT H VR I HTGDRPYVC PFDGC NK KF | | (SEQ ID NO:18) |

| | Identity (%) | Similarity (%) | Function |
|---|---|---|---|
| HATF-1 | | | ?, Associated with hypertension |
| WT- 1 | 42 | 49 | urogenital development |
| NK-10 | 54 | 73 | transcriptional repression |
| HF-10 | 56 | 66 | hematopoiedic differentiation |
| KID-1 | 41 | 61 | ?; Kidney-specific expression |

EXAMPLE 3

Figure 4:
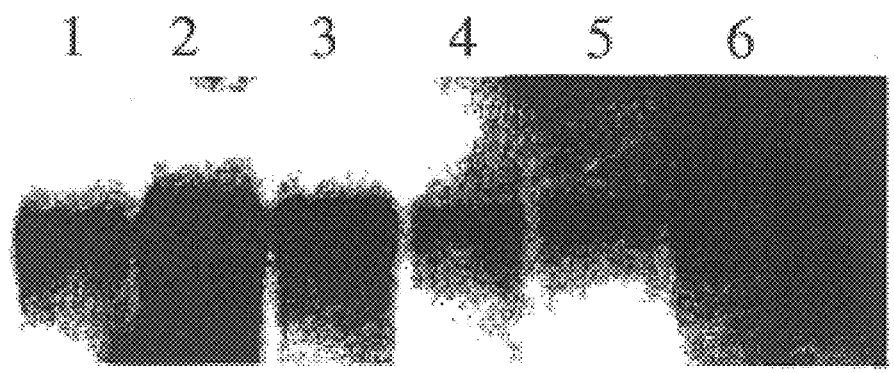
FIG. 4 depicts a gel demonstrating the differential expression of HATF-1 mRNA in the brain of hypertensive rats.

Expression of a Differentially Expressed mRNA in Neonatal SHR Brains and Tissue-culture Cells Derived from Hypertension-affected Tissues Because this differentially expressed mRNA was identified in a genetic screen comparing mRNA expression in affected tissues of hypertensive-prone and normotensive neonatal rats, Northern analysis was performed to survey mRNA expression. Confirming the results of the differential mRNA display, mRNA is expressed at 2- to 4-fold higher levels in hypertensive animals as compared to normotensive controls at several time points examined, indicating that the differential expression continues at least until day 9/10 post-partum (see FIG. 4).

Northern analysis was also used to study differences in expression levels of the HATF-1 mRNA in cultured microvascular endothelial cells (EC) derived from either hypertensive or normotensive adult rat brains. HATF-1 is prominently expressed in SHR-derived EC, a difference in expression of greater than four-fold over endothelial cells derived from pooled normotensive control brains (FIG. 5). When similar analyses were performed on adult kidney-derived mesangial cells, HATF-1 mRNA levels in SHR were three-fold higher than in WKY-derived mesangial cells (FIG. 6). Additionally, a smaller mRNA (~4 kb) not observed in whole brain or cerebrovascular endothelial cells was detected in SHR mesangial cells, indicating that tissue-specific regulation of HATF-1 mRNA expression may occur at the level of alternative splicing.

EXAMPLE 4

Tissue-specific Expression of a Hypertensive-specific mRNA

Northern analysis was carried out to determine whether expression of this hypertensive-specific transcript was confined to specific tissues. Adult SHR and WKY animals were obtained commercially; total RNA from various tissues was isolated as described above and subjected to Northern analysis using a cDNA probe constructed from the hypertensive-specific transcript. In normotensive animals the transcript is found in all the tissues examined except the liver.

EXAMPLE 5

Expression of HA TF-1 in Pre-hypertensive and Adult SHR Tissues

Polyclonal antibodies were prepared using HATF-1 polypeptides synthesized from the novel amino acid sequence, as described above. HATF-1 levels were compared in young (6 weeks old), non-hypertensive SHR (mean systolic blood pressure of 103 mm Hg) and adult male SHR (14 weeks old) already exhibiting profound hypertension SHR (mean systolic blood pressure of 185 mm Hg). Western analysis of tissues isolated from such animals reveal the presence of a 250 kD protein found uniquely in brain as well as 70 kD and 57 kD forms found in kidney and heart (FIG. 7). In SHR brain the 250 kD isoform is expressed at 20-fold higher levels as compared to the 57 kD form; the intermediate 70 kD isoform is undetectable. In 6 week SHR kidney, the 70 kD and 57 kD isoforns are detectable at a ratio of 1:5, respectively, while in 14 week SHR kidney the ratio of 70 kD to 57 kD isoforms is 4:5. These results defining alternative forms of the HATF-1 protein are consistent with the multiple mRNA species detected in SHR-derived mesangial cells, where a 4 kb form is observed in addition to the 6 kb mRNA species seen in brain and endothelium.

EXAMPLE 6

Localization of a Hypertension-associated Protein to the Nuclei of SHR Mesangial Cells To further characterize whether HATF-1 is a bona-fide transcription factor that resides within nuclei of cells derived from SHR versus WKY animals anti-HATF-1 antibodies were used to perform immunolocalization of the HATF-1 protein to the nucleus in SHR mesangial cells (FIG. 8A). Nuclear staining in SHR-derived cultured mesangial cells was observed in 82.5% of cells in randomly selected fields (165 cells out of 200 cells counted). HATF-1 protein was also localized in renal mesangial cells derived from SKY animals, but was observed in decreased abundance as a lower percentage of WKY cells stained positively for HATF-1 versus SHR mesangial cells (38.5% versus 82.5% in SHR) (FIG. 8B).

The HATF-1 protein was found at 2-fold higher levels in SHR-derived mesangial cells versus normotensive controls, as determined by Western blotting of whole cell lysates derived from SHR and WKY mesangial cells and densitometric analysis of the 57 kD and 70 kD isoforms of the protein (FIG. 9).

EXAMPLE 7

Identiftcation of the Human HATF-1 (hHA TF-1) and Mouse HATF-1 (mHA TF-1) Orthologs of Rat HATF-1

To determine whether the HATF-1 gene, originally identified in rodents, is a member of a larger multi-gene family and to ascertain specifically whether HATF-1 is expressed in humans, cDNAs were prepared by reverse transcription of total cellular RNA derived from adult human retinal pericytes grown in culture. This poly d(T) primed cDNA was used as a template for polymerase chain reaction (PCR) of the HATF-1 cDNA using gene specific primers designed from the rat HATF-1 sequence (FIG. 10A). These primers do not include any regions predicted to encode zinc finger motifs, and searching the database with such primers indicates no other homologies with any published sequences. Following 35 cycles of amplification, PCR products were purified, ligated into pGEM-T (Promega, Wis.) and sequenced. As can be seen in FIG. 11a, human HATF-1 (hHATF-1) is 100% identical to rat HATF-1 (r HATF-1) over the 313 base pair PCR product.

To clone the murine form of HATF-1 (mHATF-1), cDNA was generated from a cultured mouse cell line and processed as described above. The data indicate that mHATF-1 is 100% identical to the rat and human HATF-1 over the space of 313 base pairs.

Interestingly, another mRNA was also identified, which is distinct from, but related to mHATF-1 that is 86% identical to mHATF-1. This additional family member has been termed HATF-1 Related Protein-1 (HRP-1) (FIG. 11B). These results indicate that HATF-1 is conserved in several mammalian species, and suggest that HATF-1 and HRP-1 are but two members of a larger multi-gene family.

EXAMPLE 8

Expression of Recombinant HATF-1 and HRP-1 Protein in Bacterial Cells

In this example, HATF-1 and HRP-1 is expressed as a recombinant glutathione-S-transferase (GST) fusion polypeptide in E. coli and the fusion polypeptide is isolated and characterized. Specifically, HATF-1 and HRP-1 is fused to GST and this fusion polypeptide is expressed in E. coli, e.g., strain PEB199. Expression of the GST-HATF-1 and HRP-1 fusion protein in PEB 199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

EXAMPLE 9

Expression of Recombinant HATF-1 and HRP-1 Protein in COS Cells

To express the HATF-1 and HRP-1 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire HATF-1 and HRP-1 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the HATF-1 and HRP-1 DNA sequence is amplified by PCR using two primers. The 5' primer contains the restriction site of interest followed by approximately twenty nucleotides of the HATF-1 and HRP-1 coding sequence starting from the initiation codon; the 3' end sequence contains complementary sequences to the other restriction site of interest, a translation stop codon, the HA tag or FLAG tag and the last 20 nucleotides of the HATF-1 and HRP-1 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the HATF-1 and HRP-1 gene is inserted in the correct orientation. The ligation mixture is transformed into E. coli cells (strains HB 101, DH5a, SURE, available from Stratagene Cloning Systems, La Jolla, Calfi., can be used), the transformed culture is plated on ampicillin media plates, and resistant colonies are selected. Plasmid DNA is isolated from transformants and examined by restriction analysis for the presence of the correct fragment.

COS cells are subsequently transfected with the HATF-1 or HRP-1-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual*. 2nd, ed, Cold Spring Harbor Laboratory, Cold Spring Harbor Laboratory Press, Cold Spring Harbor, N.Y., 1989. The expression of the HATF-1 and HRP-1 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the HATF-1 and HRP-1 coding sequence is cloned directly into the polylinker of the pCDNA/Amp vector using the appropriate restriction sites. The resulting plasmid is transfected into COS cells in the manner described above, and the expression of the HATF-1 and HRP-1 polypeptide is detected by radiolabelling and immunoprecipitation using an HATF-1 and HRP-1 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising a nucleotide sequence which shares at least 87% identity to the nucleotide sequence of SEQ ID NO:1 or 3, or a complement thereof, wherein elevated levels of said nucleic acid molecule are indicative of hypertension.

2. An isolated nucleic acid molecule comprising the nucleotide sequence of SEQ ID NO: 1 or 3, or a complement thereof.

3. An isolated nucleic acid molecule comprising a fragment of at least 312 nucleotides of the nucleotide sequence of SEQ ID NO: 1 or 3, or a complement thereof, wherein elevated levels of said nucleic acid molecule are indicative of hypertension.

4. An isolated nucleic acid molecule which encodes a polypeptide comprising an amino acid sequence that shares at least 90% identity to the amino acid sequence of SEQ ID NO: 2 or 4, wherein elevated levels of said nucleic acid molecule are indicative of hypertension.

5. An isolated nucleic acid molecule which encodes a polypeptide comprising at least 50 contiguous amino acid residues of the amino acid sequence of SEQ ID NO: 2, wherein elevated levels of said nucleic acid molecule are indicative of hypertension.

6. An isolated nucleic acid molecule which encodes a polypeptide comprising at least 15 contiguous amino acid residues of the amino acid sequence of SEQ ID NO: 4, wherein elevated levels of said nucleic acid molecule are indicative of hypertension.

7. An isolated nucleic acid molecule which encodes a naturally occurring allelic variant of a polypeptide consisting or the amino acid sequence of SEQ ID NO: 2 or 4, wherein the nucleic acid molecule hybridizes to a complement of a nucleic acid molecule consisting of SEQ ID NO: 1, 3, or 5, at 6×SSC at 45° C., followed by one or more washes in 0.2×SSC, 0.1% SDS at 50–60° C., wherein elevated levels of said nucleic acid molecule are indicative of hypertension.

8. An isolated nucleic acid molecule which encodes a polypeptide comprising the amino acid sequence of SEQ ID NO:2 or 4.

9. The nucleic acid molecule of any one of claims 1, 2, 3, 4, 5, 6, 7, or 8, further comprising nucleic acid sequences encoding a heterologous polypeptide.

10. A vector comprising the nucleic acid molecule of any one of claims 1, 2, 3, 4, 5, 6, 7, or 8.

11. A host cell comprising the nucleic acid molecule of any one of claims 1, 2, 3, 4, 5, 6, 7, or 8.

12. The host cell of claim 11 which is a mammalian host cell.

13. A method for producing a polypeptide comprising culturing a host cell comprising the nucleic acid molecule of any one of claims 1, 2, 3, 4, 5, 6, 7, or 8, under conditions in which the nucleic acid molecule is expressed, thereby producing, a polypeptide encoded by the nucleic acid molecule of any one of claims 1, 2, 3, 4, 5, 6, 7, or 8.

14. A kit comprising the isolated nucleic acid molecule of any one of claims 1, 2, 3, 4, 5, 6, 7, or 8.

\* \* \* \* \*

UNITED STATES PATENT AND TRADEMARK OFFICE
CERTIFICATE OF CORRECTION

PATENT NO. : 6,521,420 B1
DATED : March 3, 2004
INVENTOR(S) : Herman et al.

It is certified that error appears in the above-identified patent and that said Letters Patent is hereby corrected as shown below:

<u>Column 1,</u>
Line 9, should read:
-- GOVERNMENT RIGHTS
This invention was made with Government support under contract numbers EY09033 and GM55110 awarded by the National Institutes of Health. The government has certain rights in this invention. --

Signed and Sealed this

Sixth Day of July, 2004

JON W. DUDAS
*Acting Director of the United States Patent and Trademark Office*